US012773526B2

(12) United States Patent
Tal

(10) Patent No.: US 12,773,526 B2
(45) Date of Patent: Oct. 27, 2026

(54) VASCULAR ACCESS CATHETER

(71) Applicant: Michael Gabriel Tal, Tel Aviv (IL)

(72) Inventor: Michael Gabriel Tal, Tel Aviv (IL)

(73) Assignee: Embrace Medical Ltd., Tel Aviv (IL)

( * ) Notice: Subject to any disclaimer, the term of this patent is extended or adjusted under 35 U.S.C. 154(b) by 0 days.

(21) Appl. No.: 17/927,154

(22) PCT Filed: May 25, 2021

(86) PCT No.: PCT/US2021/034016
§ 371 (c)(1),
(2) Date: Nov. 22, 2022

(87) PCT Pub. No.: WO2021/242734
PCT Pub. Date: Dec. 2, 2021

(65) Prior Publication Data

US 2023/0191085 A1 Jun. 22, 2023

Related U.S. Application Data

(60) Provisional application No. 63/030,410, filed on May 27, 2020.

(51) Int. Cl.
*A61M 25/00* (2006.01)
*A61M 25/06* (2006.01)
*A61M 39/02* (2006.01)

(52) U.S. Cl.
CPC .... *A61M 25/0068* (2013.01); *A61M 25/0606* (2013.01); *A61M 2039/0258* (2013.01); *A61M 2039/0276* (2013.01)

(58) Field of Classification Search
CPC .......... A61M 25/0068; A61M 25/0606; A61M 2039/0258; A61M 2039/0276;
(Continued)

(56) References Cited

U.S. PATENT DOCUMENTS 1,879,249 A 9/1932 Coy
4,617,019 A * 10/1986 Fecht ................ A61M 25/0021
604/274

(Continued)

FOREIGN PATENT DOCUMENTS

CN 107913445 A 4/2018
EP 1321163 A1 6/2003

(Continued)

OTHER PUBLICATIONS

International Preliminary Report on Patentability Chapter II mailed on Jun. 1, 2022 in PCT/US2021/034016.

(Continued)

*Primary Examiner* — Chelsea E Stinson
*Assistant Examiner* — Hamza A Darb
(74) *Attorney, Agent, or Firm* — Veros Legal Solutions, LLP

(57) ABSTRACT

Vascular access catheter comprising elongated tubular catheter body enclosing a lumen. Catheter body includes catheter tip ending with a catheter distal end and comprising a distal edge at the catheter distal end surrounding an opening opened to the lumen. The distal edge includes a front edge portion spanning a top portion of the opening and an inclined edge portion spanning a bottom portion of the opening and inclining proximally away from the front edge portion, relative to a longitudinal axis of the catheter body. The vascular access catheter can be provided in a vascular access kit further comprising access needle with hollow needle body and beveled tip ending with sharp needle edge.

31 Claims, 16 Drawing Sheets

(58) Field of Classification Search

CPC ...... A61M 25/0637; A61M 2025/0687; A61M 25/0074; A61M 25/0073; A61M 2025/0073; A61M 25/0069

See application file for complete search history.

(56) References Cited

U.S. PATENT DOCUMENTS

| | | | | |
|---|---|---|---|---|
| 4,661,300 | A | 4/1987 | Daugherty | |
| 4,904,433 | A | 2/1990 | Williamitis | |
| 4,919,605 | A | 4/1990 | Kousai et al. | |
| 5,057,083 | A | 10/1991 | Gellman | |
| 5,102,324 | A | 4/1992 | Bullard et al. | |
| 5,352,205 | A | 10/1994 | Dales et al. | |
| 5,484,565 | A | 1/1996 | Larsen et al. | |
| 5,531,701 | A | 7/1996 | Luther | |
| 5,716,572 | A | 2/1998 | Lesiczka et al. | |
| 5,843,356 | A | 12/1998 | Patel et al. | |
| 5,857,464 | A | 1/1999 | Desai | |
| 5,985,195 | A | 11/1999 | Muskatello | |
| 6,596,011 | B2 | 7/2003 | Johnson et al. | |
| 6,740,277 | B2 | 5/2004 | Howell et al. | |
| 6,979,318 | B1 | 12/2005 | McDonald et al. | |
| 7,029,467 | B2 | 4/2006 | Currier et al. | |
| 7,959,595 | B2 | 6/2011 | Melsheimer et al. | |
| 8,936,581 | B2 | 1/2015 | Bihlmaier | |
| 9,078,994 | B2 | 7/2015 | Rosenman et al. | |
| 9,757,536 | B2 | 9/2017 | Abt et al. | |
| 9,987,423 | B2 | 6/2018 | Kuracina et al. | |
| 10,478,592 | B2 | 11/2019 | Shevgoor | |
| 10,610,668 | B2 | 4/2020 | Burkholz et al. | |
| 2005/0090852 | A1 * | 4/2005 | Layne | A61F 2/4601 604/103.05 |
| 2009/0076435 | A1 | 3/2009 | Melsheimer et al. | |
| 2010/0137804 | A1 | 6/2010 | Wiley | |
| 2010/0217234 | A1 | 8/2010 | Grovender et al. | |
| 2012/0065569 | A1 | 3/2012 | Steegers et al. | |
| 2015/0038908 | A1 | 2/2015 | Antonucci | |
| 2019/0038876 | A1 | 2/2019 | Isaacson et al. | |
| 2019/0038877 | A1 | 2/2019 | Isaacson et al. | |
| 2019/0381282 | A1 * | 12/2019 | Ishida | A61M 25/0052 |
| 2020/0188632 | A1 | 6/2020 | Burkholz et al. | |
| 2022/0257902 | A1 | 8/2022 | Tal | |
| 2023/0191085 | A1 | 6/2023 | Tal | |

FOREIGN PATENT DOCUMENTS

| | | | | |
|---|---|---|---|---|
| JP | 2004057516 | A | 2/2004 | |
| JP | 2005169012 | A | 6/2005 | |
| JP | 2006055674 | A | 3/2006 | |
| WO | 2009131583 | A1 | 10/2009 | |
| WO | WO-2018169032 | A1 * | 9/2018 | A61M 25/0052 |
| WO | 2020059388 | A1 | 3/2020 | |

OTHER PUBLICATIONS

International Search Report and Written Opinion, mailed Nov. 16, 2021 in PCT/US2021/034016.

Notice of Reasons for Refusal mailed on Feb. 15, 2024 in JP 2022-572483.

Extended European Search Report mailed on May 29, 2024 in EP 21814216.4.

Communication pursuant to Rules 70(2) and 70a(2) EPC mailed on Jun. 18, 2024 in EP 21814216.4.

Notice of Allowance mailed on Nov. 18, 2024 in JP 2022-572483.

Office Action mailed on Sep. 29, 2024 in CN 202180037980.0.

Office Action mailed on Jun. 6, 2025 in CN 202180037980.0.

* cited by examiner

VASCULAR ACCESS CATHETER

CROSS-REFERENCE TO RELATED APPLICATIONS

This application claims the benefit of U.S. Provisional Patent Application No. 63/030,410, filed on May 27, 2020, titled OVER-THE-NEEDLE CATHETER, the entire contents of which are hereby incorporated by reference herein.

FIELD OF THE INVENTION

The present disclosure relates to devices and methods for accessing a blood vessel, and more particularly, but not exclusively, to devices and methods for inserting a catheter into a blood vessel over an access needle.

BACKGROUND OF THE INVENTION

Peripheral intravenous (PIV) catheter insertion is an invasive hospital procedure for administrating medication or other fluids, commonly involves needle insertion into a peripheral vein followed by introduction of the catheter over the needle. For fluid administration the needle is withdrawn, leaving at least the catheter tip and opening patent for fluid delivery. PIV catheterization traditionally involves substantial failure rates indicated by removal of the catheter from the vein before the end of its intended dwell time. Common reasons for failure include "infiltration", in which the catheter and/or needle penetrates vein wall portion opposing the entry point to the vein, and "occlusion" which is loss of ability to infuse due to thrombosis in the catheter or vein itself, optionally due to infiltration and vein inflammation (phlebitis).

SUMMARY OF THE INVENTION

The present disclosure relates to devices and methods for accessing a blood vessel, and more particularly, but not exclusively, to devices and methods for inserting a catheter into a blood vessel over an access needle.

In certain embodiments, there is provided a vascular access catheter comprising an elongated tubular catheter body enclosing a lumen. The catheter body includes a catheter tip ending with a catheter distal end and comprising a distal edge at the catheter distal end surrounding an opening opened to the lumen. The distal edge includes a front edge portion spanning a top portion of the opening and an inclined edge portion spanning a bottom portion of the opening and inclining proximally away from the front edge portion, relative to a longitudinal axis of the catheter body.

In some embodiments, the lumen is cylindrical along a portion of the catheter body proximally to the catheter tip and tapers along a portion of the catheter tip.

In some embodiments, the front edge portion substantially coincides with a transverse plane of the catheter body crossing perpendicularly to the longitudinal axis. In some embodiments, the front edge portion spans at least half of a cross section of the catheter body at the distal end parallel to the transverse plane. In some embodiments, the inclined edge portion is inclined to the transverse plane or to the front edge portion at an average angle smaller than 45°.

In some embodiments, the front edge portion is at least partially flat. In some embodiments, the inclined edge portion is at least partially curved.

In some embodiments, radius of curvature of the inclined edge portion is smallest adjacent to the front edge portion and/or greatest adjacent to a vertex of the inclined edge portion. In some embodiments, radius of curvature of the inclined edge portion gradually increases between the front edge portion and a vertex of the inclined edge portion.

In some embodiments, the inclined edge portion includes or merges with a sliding surface, the sliding surface is at least partially parallel, or inclined at a shallow angle, to the inclined edge portion and/or to the longitudinal axis. In some embodiments, the sliding surface forms a shaped area bounded by and between a distal parabola and a proximal parabola, the distal parabola has a smaller focal length than the proximal parabola. In some embodiments, the sliding surface is at least partially curved. In some embodiments, the catheter tip varies in thickness along the sliding surface. In some embodiments, the sliding surface has an average radius of curvature substantially greater than a radius of an outer surface portion of the catheter tip opposing the sliding surface in a mutual transverse cross section.

In some embodiments, the inclined edge portion includes two curved surfaces provided at opposite sides of the opening relative to the longitudinal axis, each one of the sliding surfaces distinctly merges with the front edge portion at a different merging portion.

In some embodiments, the catheter is configured to engage an inner surface of a blood vessel with the inclined edge portion when pushed over an access needle, and to slide with the inclined edge portion distally on the inner surface of the blood vessel when the catheter tip is pressed against the blood vessel wall when the access needle is withdrawn from the catheter tip.

In some embodiments, the front edge portion merges with the inclined edge portion at a merging portion, wherein the merging portion is rounded, curved and/or inclined.

In some embodiments, the merging portion is located adjacent to or below the longitudinal axis.

In some embodiments, the catheter tip includes a groove extending along a bottom end of the catheter tip, proximally from, and opened to, the inclined edge portion. In some embodiments, the catheter tip includes a narrow cut or a slit extending along a bottom end of the catheter tip, proximally from, and opened to, the inclined edge portion.

In some embodiments, the inclined edge portion, adjacent to a vertex thereof, forms a first tangential angle with the longitudinal axis being smaller than about 20°. In some embodiments, the inclined edge portion, adjacent to the front edge portion, forms a second tangential angle with the longitudinal axis being greater than about 45°.

In some embodiments, a bottom end of the catheter tip has elastic resistance to inward radial deformation smaller than the top end of the catheter tip. In some embodiments, the catheter tip is configured, when not internally supported with an access needle, to collapse radially inwardly when a bottom end of the catheter tip is pressed at an angle against a blood vessel wall, when the catheter body transfers to the blood vessel wall a force insufficient for causing mechanical damage thereto.

In some embodiments, the catheter is configured such that the catheter tip along a bottom end thereof, when radially inwardly collapsed, has a footprint on a surface of the blood vessel wall greater in size than a maximal sized cross section of the access needle.

In certain embodiments, there is provided a vascular access kit, comprising the vascular access catheter and an access needle comprising a hollow needle body and a beveled tip ending with a distal sharp needle edge. In some embodiments, the catheter is configured to accommodate the access needle through the lumen and the opening in at least two configurations comprising a tissue-penetration configuration wherein the beveled tip fully extends from the lumen distally to the catheter distal end, and a safety configuration wherein the beveled tip fully resides within the lumen proximally to the catheter distal end.

In some embodiments, the lumen decreases in diameter along the catheter tip to a sealing diameter smaller than a diameter of the access needle proximally to the beveled tip, so as to form a seal around the access needle for preventing blood from accessing the lumen via the opening when in the tissue-penetration configuration and to facilitate access of blood into the lumen via the opening when in the safety configuration.

In some embodiments, the kit comprising coupling means configured to fixate the access needle in the catheter in the tissue-penetration configuration.

In some embodiments, when in the tissue-penetration configuration, the needle edge has an equal or greater distance to a vertex of the inclined edge portion than to a vertex of the front edge portion.

In some embodiments, the kit is configured such that the catheter tip along a bottom end thereof, when radially inwardly collapsed, has a footprint on a surface of the blood vessel wall greater in size than a maximal sized lesion formable in the blood vessel wall by the access needle.

In certain embodiments, there is provided a method for inserting a catheter into a blood vessel using the kit, the method comprising: inserting the catheter tip into the blood vessel when the catheter and the access needle are in the tissue-penetration configuration; shifting the catheter and the access needle to the safety configuration by moving the beveled tip relative to the catheter tip, such that the beveled tip fully resides within the lumen proximally to the catheter distal end; engaging an inner surface of the blood vessel with the inclined edge portion; removing the access needle from the lumen; and advancing the catheter distally in the blood vessel.

In some embodiments, the inserting includes forming a lesion through the inner surface of the blood vessel wall with the beveled tip, wherein the engaging includes sliding over remote portions of the inner surface from opposite sides of the lesion with the inclined edge portion, and wherein the advancing includes sliding over and across the lesion with the inclined edge portion and/or the catheter tip along a bottom end thereof.

In some embodiments, the inserting includes and/or follows verifying if blood is drawn from the blood vessel into the access needle. In some embodiments, if the verifying results in annulling blood drawn into the access needle, the shifting is followed by withdrawing the catheter until verifying blood is drawn from the blood vessel into the lumen. In some such embodiments, the withdrawing follows the shifting or the removing and precedes the engaging.

In some embodiments, the engaging follows verifying blood is drawn from the blood vessel into the lumen after the shifting.

In some embodiments, the inserting includes verifying the catheter is fixated to the access needle in the tissue-penetration configuration; and penetrating the blood vessel with the beveled tip to allow blood drawing into the access needle from the blood vessel. In some embodiments, the inserting includes verifying the bottom portion is directed towards, and/or the top portion is directed away from, the blood vessel.

In some embodiments, the inserting includes and/or follows verifying that the blood vessel is diseased and/or is a vein equal to or smaller in diameter than catheter body or than about 1 mm.

All technical or/and scientific words, terms, or/and phrases, used herein have the same or similar meaning as commonly understood by one of ordinary skill in the art to which the invention pertains, unless otherwise specifically defined or stated herein. Illustrative embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

BRIEF DESCRIPTION OF THE DRAWINGS

Some embodiments are herein described, by way of example only, with reference to the accompanying drawings. With specific reference now to the drawings in detail, it is stressed that the particulars shown are by way of example and for purposes of illustrative description of some embodiments. In this regard, the description taken together with the accompanying drawings make apparent to those skilled in the art how some embodiments may be practiced.

In the drawings.

DETAILED DESCRIPTION

Certain embodiments relate to devices and methods for accessing a blood vessel, and more particularly, but not exclusively, to devices and methods for inserting a catheter into a blood vessel over an access needle.

In some embodiments, the catheter has a catheter tip ending with a distal edge that has different structural and/or functional features over a top portion of the catheter tip versus over a bottom portion of the catheter tip, such that the catheter tip is configured to interact differently with an internal wall surface of the blood vessel when engaging the blood vessel wall with the bottom portion than with the top portion of the catheter tip, under same forces and conditions, when the catheter tip is not internally supported by the needle. In some embodiments, the catheter tip bottom portion is constructed and/or shaped differently than the catheter tip top portion close to the distal edge. In some such or other embodiments, the distal edge is shaped differently closer to the bottom portion than to the top portion of the catheter tip.

Figure 1A:
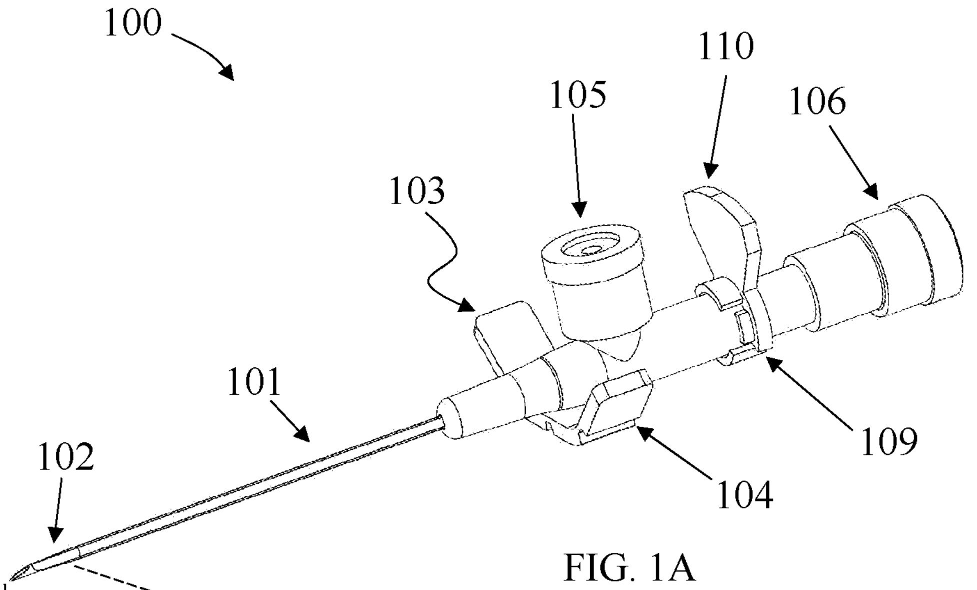
FIGS. 1A-1B illustrate an exemplary over-the-needle catheter, according to some embodiments.
Figure 1B:
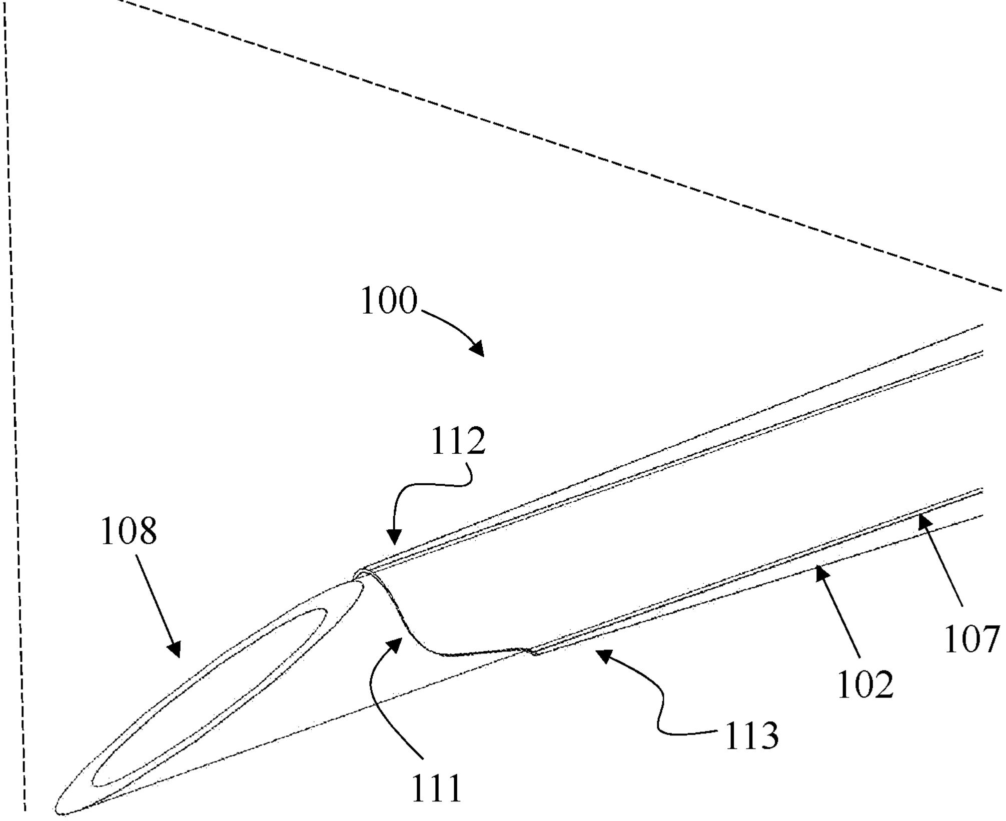

FIGS. 1A-1B illustrate an exemplary over-the-needle catheter 100 configured for example as a peripheral intravenous catheter. Catheter 100 includes a catheter elongated body 101 ending with a catheter tip 102 and connected with proximal end thereof to a catheter handheld portion 103. Handheld portion 103 includes wings 104 configured for manual handling and/or for catheter securing to patient's body such as by using adhesives. Handheld portion also 103 optionally includes a syringe connector 105 configured for connecting to a syringe for facilitating injection of fluids (e.g., medication).

Catheter 100 may be provided in a kit for peripheral intravenous access, also comprising an access needle 107. As shown, needle 107 is configured to extend through lumen of catheter body 101, and needle tip 108 thereof is configured to fully protrude distally from catheter tip 102 when access needle 107 fully extends through and properly secured to handheld portion 103 and oriented (rotationally) relative thereto using needle securing and/or orienting member 109. Connected to a proximal end of access needle 107 is a line connector 106 which is configured for connecting to a syringe and/or optionally to an intravenous infusion line. Needle 107 can be partially or fully withdrawn (in a proximal direction) relative to catheter tip 102 after detaching from handheld portion 103 and pulling access needle 107 with needle wing 110.

As shown in FIG. 1B, catheter tip 102 has a distal edge 111 between a top portion 112 and a bottom portion 113 of catheter tip 102, wherein distal edge 111 is shaped and/or configured differently adjacent to bottom portion 113 than adjacent to top portion 112.

In some embodiments, the catheter can be inserted into a blood vessel using one or more of the following steps (not necessarily in same order):

- verifying that the catheter is positioned properly such that its outer surface along the bottom portion of the catheter tip is directed towards the blood vessel, and/or that its outer surface along the top portion of the catheter tip is directed away from the blood vessel;
- inserting an access needle into the blood vessel until blood enters the access needle and can be seen in an optional flashback chamber which can be provided with the kit or integrated in the catheter or parts thereof;
- pushing the access needle with the catheter, or pushing the catheter over the access needle, towards an inner (e.g., deeper) surface of a wall of the blood vessel while the catheter tip is internally supported by the access needle;
- moving the catheter body relative to the access needle, such that a tip of the catheter is unsupported internally by the access needle (commonly resulting in that blood becomes visible inside the catheter between the catheter tube and the needle);
- engaging the inner surface with the bottom portion of the catheter tip and/or with a portion of the distal edge close to the bottom portion; and
- sliding on the inner surface by advancing the catheter distally into the blood vessel.

Figure 2A:
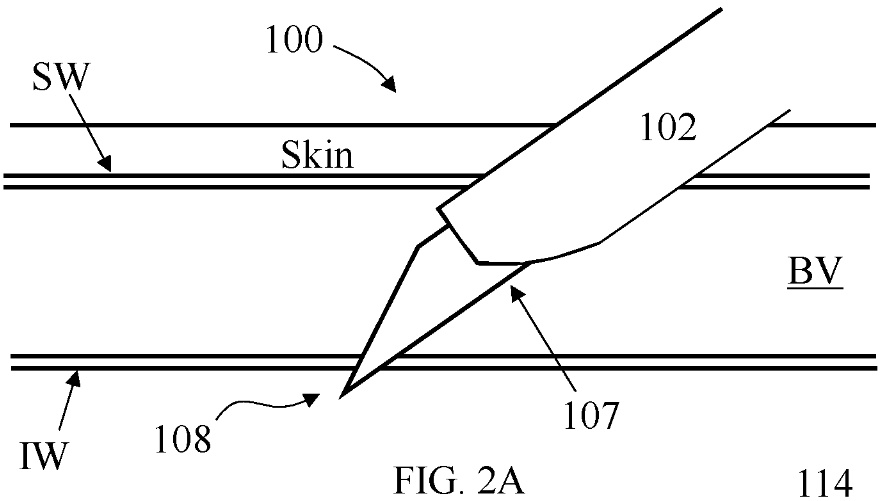
FIGS. 2A-2C schematically illustrate exemplary scenarios representing steps in a method for inserting an exemplary catheter over a needle into a blood vessel, according to some embodiments.
Figure 2B:
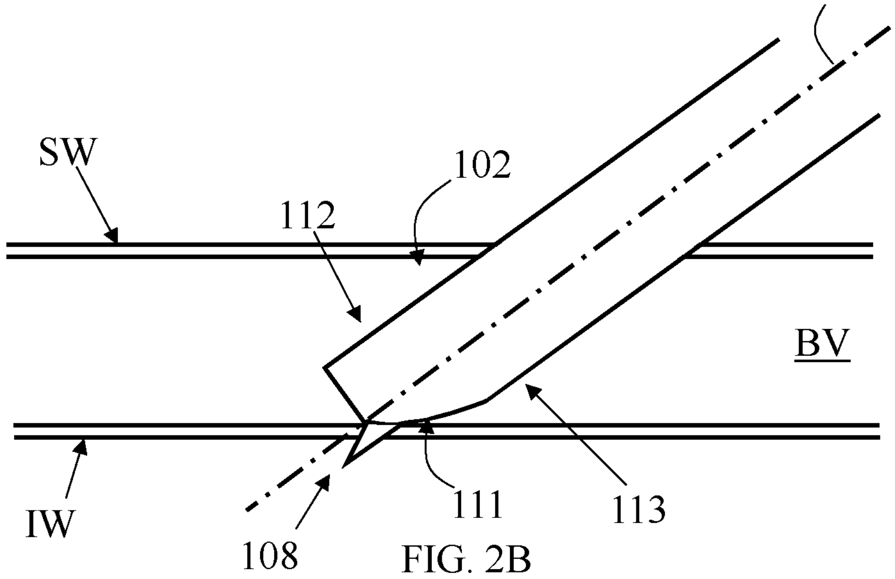
Figure 2C:
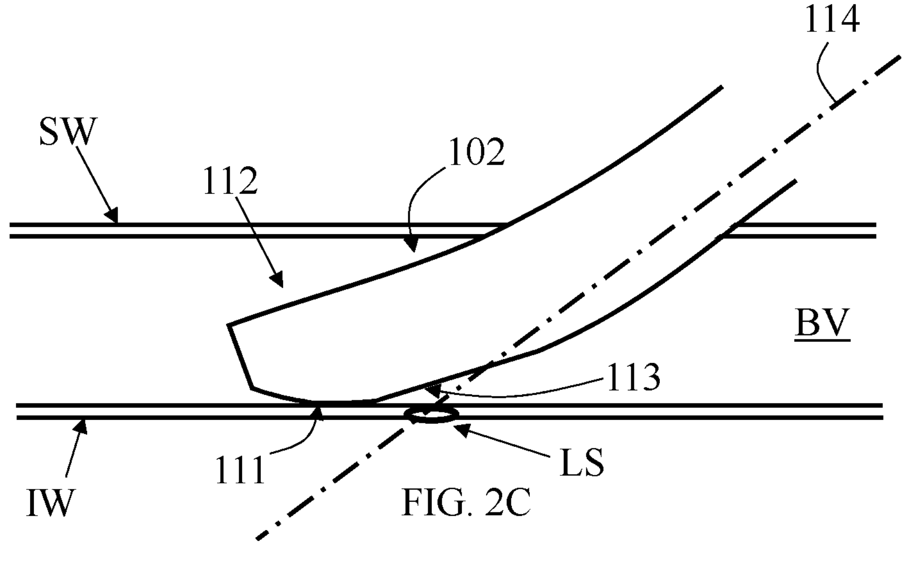

FIGS. 2A-2C schematically illustrate exemplary scenarios representing steps in a method for inserting catheter 100 over access needle 107 into a blood vessel BV. FIG. 2A shows a first scenario following penetration of catheter 100 into blood vessel BV. The sharp needle tip 108 is applied to penetrate through skin and an outer (e.g., shallower) wall portion SW of blood vessel BV, with catheter tip 102 surrounding needle 107 and located proximally to needle tip 108. FIG. 2B shows an optional second scenario in which catheter tip 102 is advanced with or over access needle 107 until engaging an inner (e.g., deeper) wall portion IW of blood vessel BV generally opposing outer wall portion SW. FIG. 2C shows a third scenario in which needle 107 is partially or fully withdrawn relative to catheter tip 102 and the latter is further advanced distally in blood vessel BV while optionally flexing and/or sliding over inner wall portion IW.

A common failure involved in initial needle and catheter penetration into blood vessels, especially small ones, is forming of an unintentional cut or lesion, such as lesion LS (shown in FIG. 2C) on inner wall portion IW of blood vessel BV with the needle tip. In such a case, when a regular catheter tip is pushed forward (distally) over a needle similar to access needle 107, it has substantial potential to further harm blood vessel BV, such as by enlarging or disintegrating lesion LS, and/or to penetrate out of the lumen of blood vessel BV through lesion LS. Therefore, in some embodiments, catheter tip 102 is configured to engage with inner wall portion IW sufficiently distant from (e.g., distally to) the initial trajectory of access needle 107 which aligns with needle's longitudinal axis 114, immediately following penetration into blood vessel BV, so as to reduce likelihood of contacting a possible lesion such as lesion LS on inner wall IW formable by needle tip 108. In some such or other embodiments, catheter tip 102 is configured with a curved bottom portion of distal edge 111 and/or a bottom portion configured for inwardly collapsing, for increasing footprint on inner wall IW being sufficiently greater that dimensions of lesion LS thereby reducing likelihood it will penetrate through the lesion. In some such or other embodiments, catheter tip 102 is configured to flex forward (e.g., distally) relative to needle axis 114, as shown in FIG. 2C for example, when catheter tip 102 is unsupported, at least partially, by needle 107, such as when needle tip 108 is partially or fully withdrawn (proximally) relative thereto.

Figure 3A:
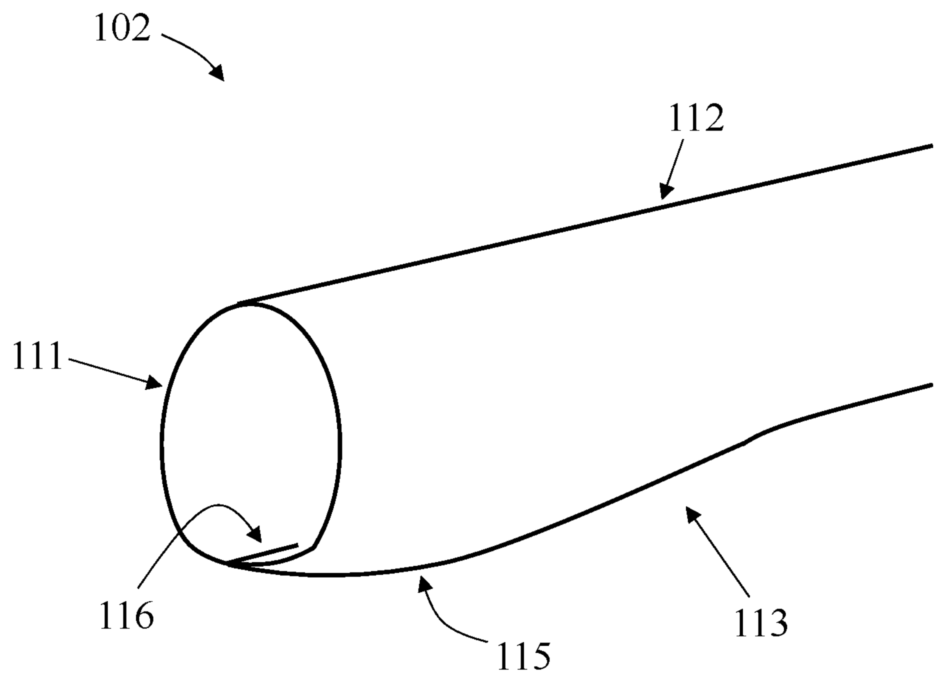
FIGS. 3A-3D schematically illustrate views of a first exemplary tip of an over-the-needle catheter, according to some embodiments.
Figure 3B:
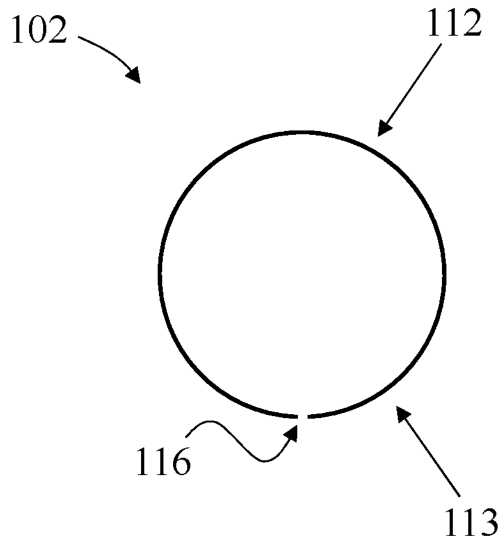
Figure 3C:
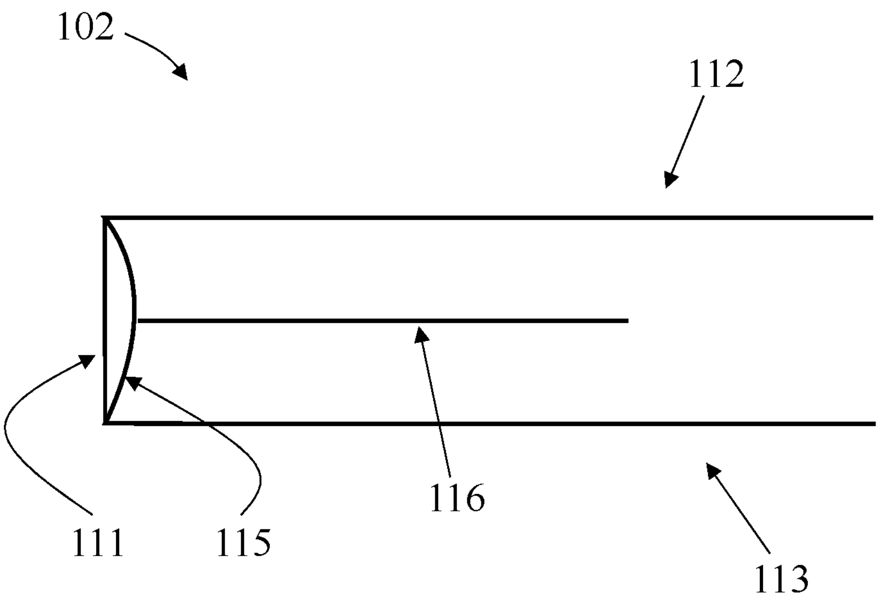

FIGS. 3A-3C schematically illustrate views of a first exemplary configuration of catheter tip 102 in an elastically relaxed (unstressed) state, in accordance with some embodiments. FIG. 3A shows an isomeric view of catheter tip 102, FIG. 3B shows a front view thereof, and FIG. 3C shows a bottom view thereof. As previously described, catheter tip 102 includes a bottom portion 113 opposing a top portion 112, about distal edge 111. Distal edge 111 optionally includes an at least one inclined edge portion optionally configured as a curved and/or beveled inclined edge portion 115 which is inclining between a more distally protruding portion of distal edge 111 and a less distally protruding portion of the distal edge, closer to bottom portion 113 than the more distally protruding portion. Distal edge 111 may be tapered at least in part thereof, for easing penetration through skin and blood vessel outer wall SW when pushed forward with access needle 107.

Bottom portion 113 is configured for engaging a wall of a blood vessel prior to top portion 112 when catheter body 101 is inclined to the blood vessel wall. In some embodiments, bottom portion 113 has elastic resistance to inward radial deformation being smaller than equivalent resistance of the top portion 112 and/or of other portions of the catheter tip 102 which are adjacent to bottom portion 113.

As a result of this design, catheter tip 102 is configured, when not internally supported with the access needle 107, to collapse (e.g., bend, compress or flex, for example) radially inwardly, when the bottom portion 113 is pressed at an angle against the blood vessel wall, when the catheter body 101 transfers to the blood vessel wall a force insufficient for causing mechanical damage thereto. When collapsed, bottom portion 113 has a footprint (i.e., contact area during or immediately after collapsing) on the surface of the blood vessel wall which is greater in size than a maximal sized lesion formable in the blood vessel wall by the access needle. Since that maximal size of needle formed lesion on the blood vessel wall is commonly about the size of needle tip 108 cross section, or less, catheter tip 102 can be designed and configured with a minimal footprint (under same reasonable forces and conditions) being greater in size than a maximal sized cross section of the access needle 107.

While being configured to collapse when pressed with bottom portion 113, catheter tip 102 is configured to sustain a substantially circular (or another generally rounded) shaped cross section when top portion 112 is pressed at an angle against the lesion, when transferring the same force to the blood vessel wall. In any event, catheter tip is configured to elastically regain its nominal circular (or another generally rounded) shaped cross section when the radially inwardly collapsed bottom portion 113 is released from external force applied thereto and returns to elastically relaxed (unstressed) state. Unlike the described difference in elastic resistance to radial compression, the bottom portion 113 optionally has elastic resistance to axial compression similar to that of the top portion 112.

Possible ways for acquiring structural and/or functional configuration causing this difference in elastic resistance to radial compression between top portion 112 and bottom position 113 of catheter tip 102, may include different mechanical, thermal and/or chemical treatment to each one of these portions, applying coating of different types or thickness for example, using different materials, or otherwise as known in relevant practice. For example, bottom portion 113 may be formed separately than the top portion 112 (or the entire remaining portion of catheter body 101), optionally of a different material or under different process or treatment than top portion 112, and later connected, such as by using adhesive or heat bonding, to the remaining catheter body 101.

Figure 3D:
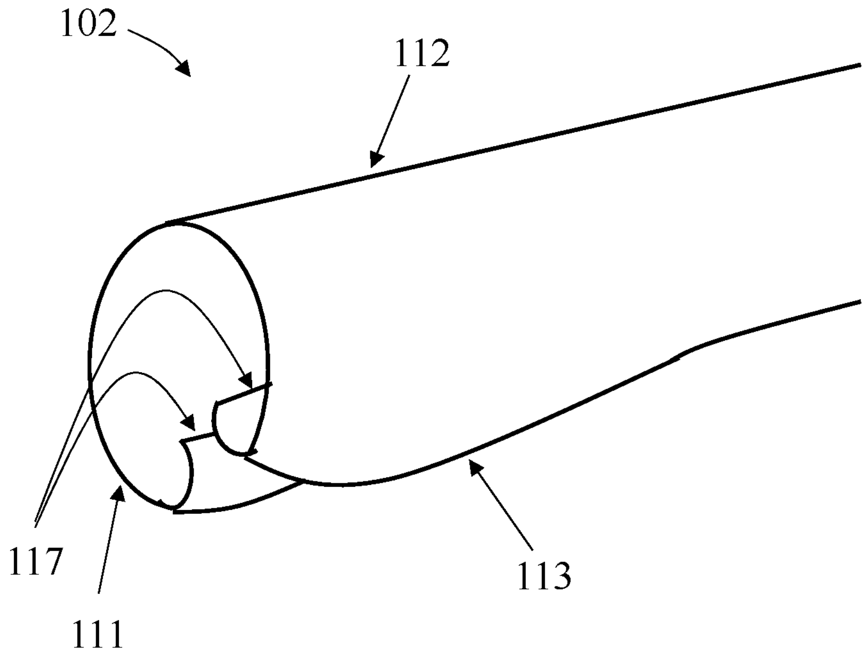

As shown, bottom portion 113 has at least one slit 116 extending from and opened to distal edge 111. Adding a slit causes a local decrease in elastic resistance to radial compression which is greater closer to the slit. Slit 116 forms opposing vertical edges 117 configured to turn inwardly towards the longitudinal axis 114 when bottom portion 113 is pressed radially inwardly, as shown in FIG. 3D, for example. Slit 116 is substantially straight and parallel to longitudinal axis 114, so that to preserve similar (e.g., same) resistance to axial compression adjacent to slit 116 as in top portion 112. Optionally, instead or in combination of a slit, bottom portion 113 has at least one weakening line extending therealong for reducing local structural resistance to radial compression relative to the top portion 112. The weakening line is optionally configured with reduced thickness and/or reduced structural strength relative to adjacent portions of bottom portion 113.

Figure 4A:
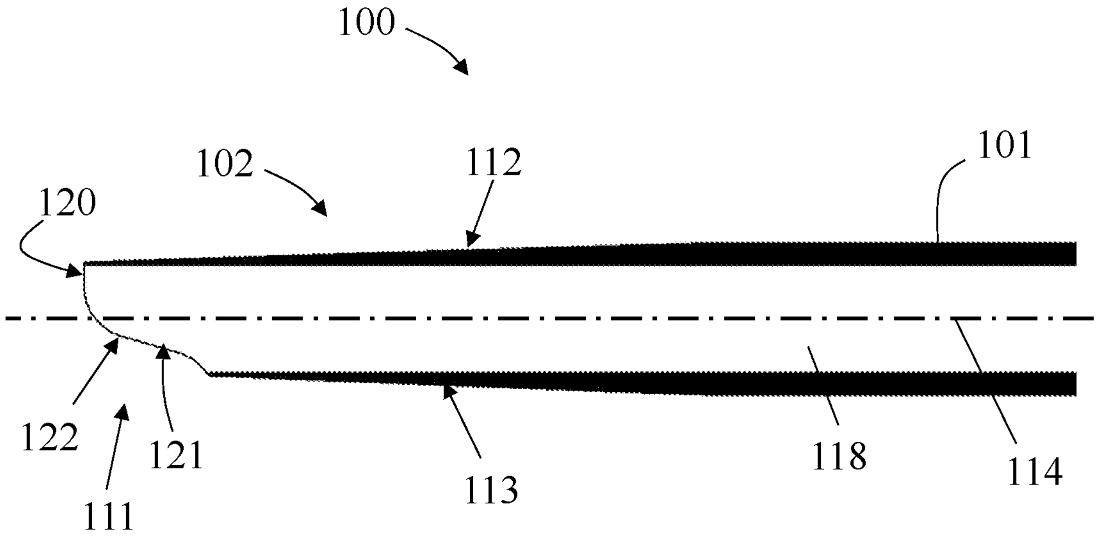
FIGS. 4A-4B schematically illustrate views of a second exemplary tip of an over-the-needle catheter, according to some embodiments.
Figure 4B:
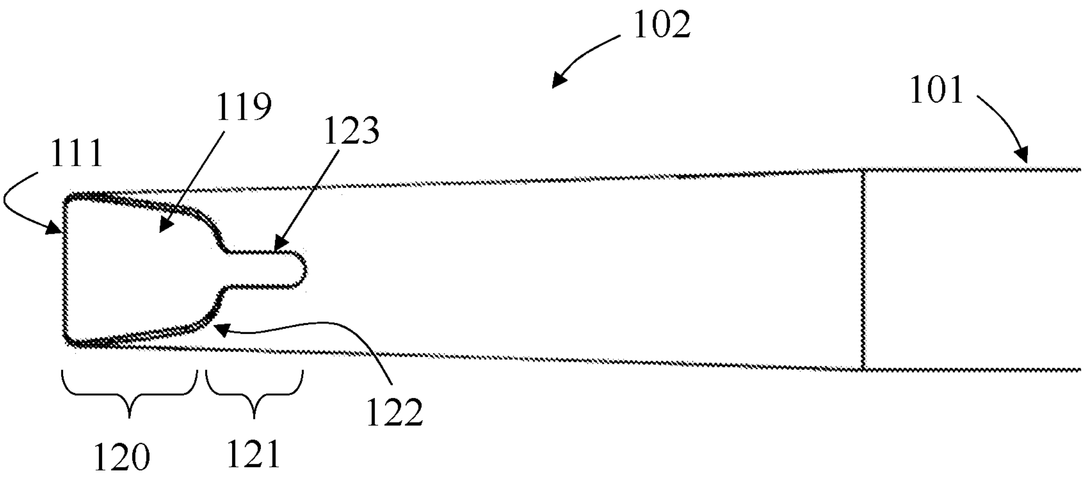

FIGS. 4A-4B schematically illustrate views of another exemplary configuration of catheter tip 102, according to some embodiments. FIG. 4A shows a side cut view of catheter tip 102, and FIG. 4B shows a bottom view thereof. As shown, catheter body 101 encloses a lumen 118, and catheter tip 102 that ends with distal edge 111 forming an opening 119 to the lumen 118 between top portion 112 and bottom portion 113. In this exemplary configuration, distal edge 111 includes a front edge portion 120 extending from top portion 112 towards bottom portion 113 substantially perpendicularly to longitudinal axis 114, and an at least one inclined edge portion optionally configured as an inclined edge portion 121 which is extending from bottom portion 113, inclined to longitudinal axis 114, towards front edge portion 120 and merges with front edge portion 120 at a merging portion 122 which is optionally located inferiorly to longitudinal axis 114 (that coincides with centerline of catheter body 101), or adjacent thereto.

As such, catheter 100 is configured to engage an inner surface of a blood vessel (as shown in FIGS. 2) with the inclined edge portion 121, when pushed over access needle 107. Also, inclined edge portion 121 is configured to slide distally on the blood vessel inner surface when catheter tip 102 is pressed against the blood vessel wall with access needle 107 withdrawn relative thereto. Optionally, catheter 100 is further configured to engage the blood vessel inner surface with inclined edge portion 121 proximally to access needle 107.

Inclined edge portion 120 is curved and forms an angle with longitudinal axis 114 adjacent to bottom portion 113 (which is optionally about 20° or less) substantially smaller than adjacent to front edge portion 120 (which is optionally about 45° or more).

Bottom portion 113 includes a groove 123 extending proximally from, and opened to, the inclined edge portion 121, optionally in a form of a narrow cut, although it may include, additionally or alternatively, at least one slit. In some embodiments, catheter tip 102 is tapered and decreases in outer diameter and/or in thickness towards distal edge 111, in order to ease penetration of the catheter into the skin and to the blood vessel.

Figure 5A:
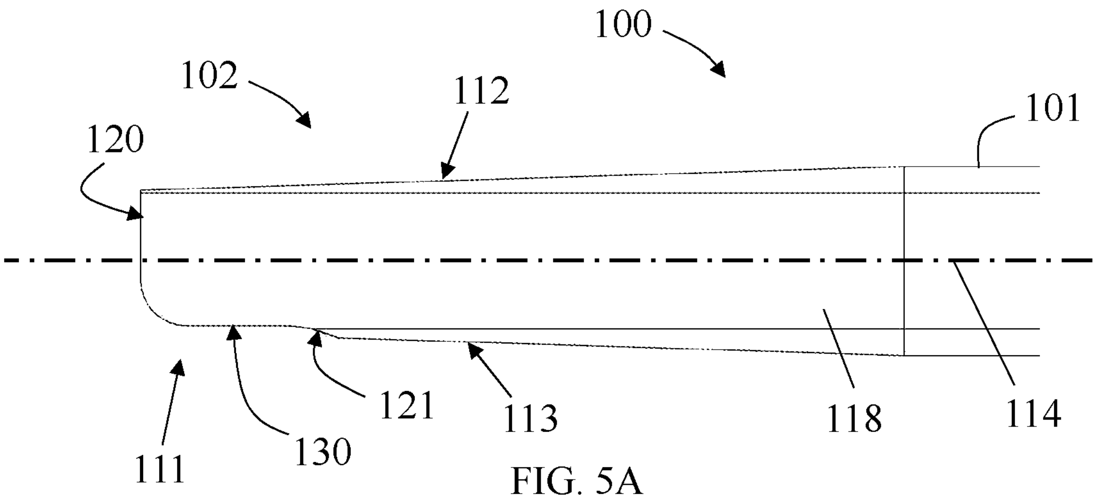
FIGS. 5A-5E schematically illustrate views of a third exemplary tip of an over-the-needle catheter, according to some embodiments.
Figure 5B:
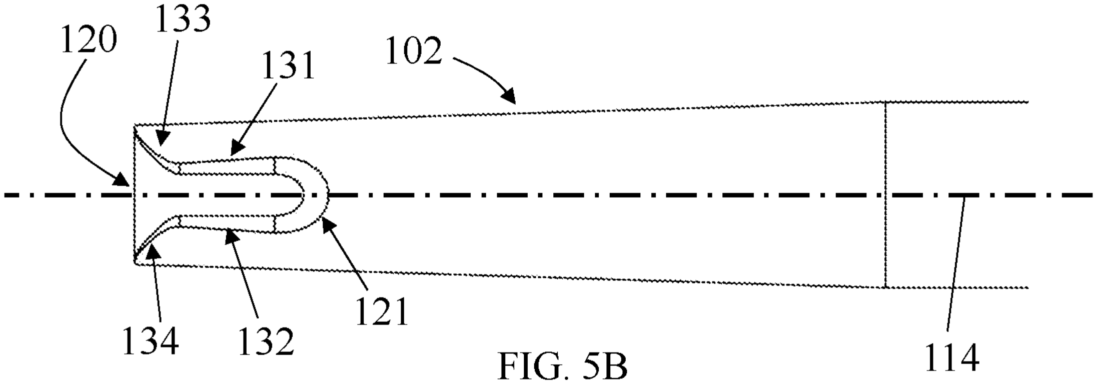
Figure 5C:
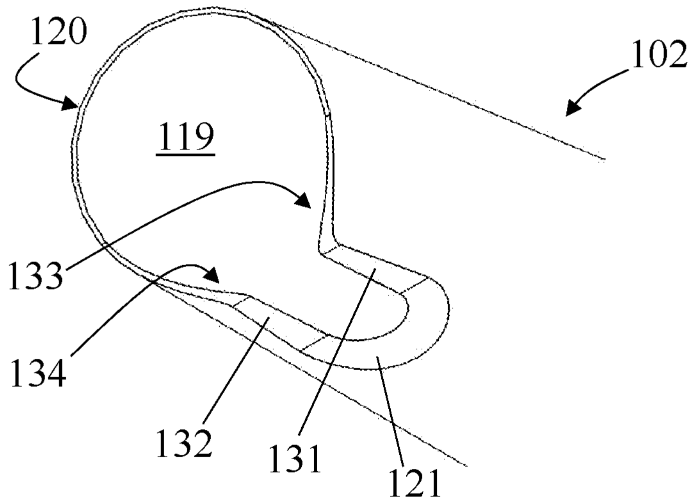
Figure 5D:
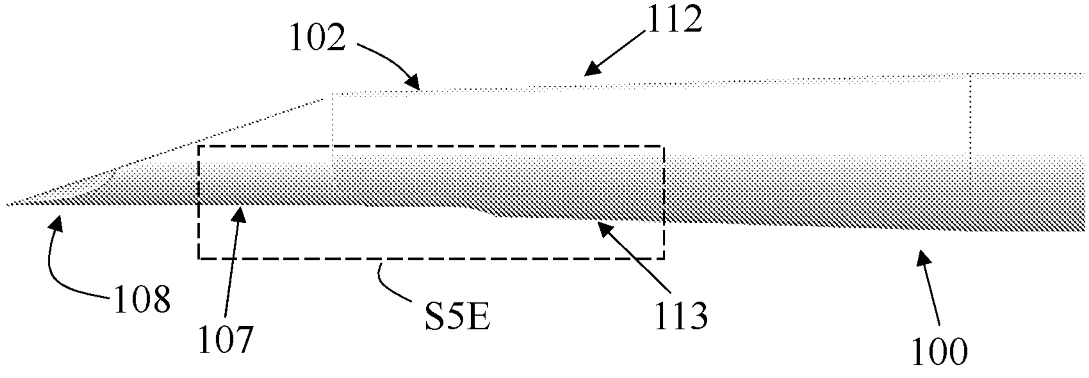
Figure 5E:
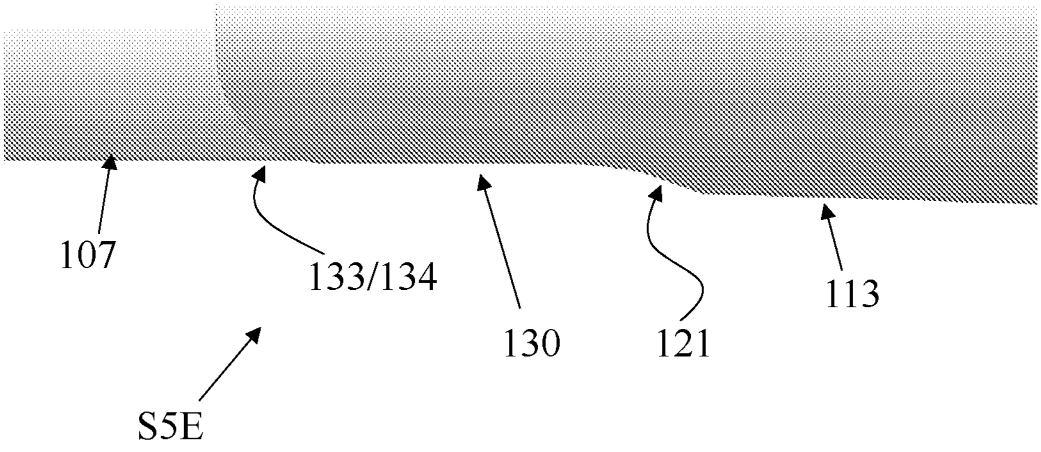

Reference is made to FIGS. 5A-5E schematically illustrate views of a third exemplary configuration of tip 102, according to some embodiments. FIG. 5A and FIG. 5B show a side cut view and a bottom view of catheter tip 102, respectively; FIG. 5C shows a axonometric projection view of a frontal (distal) portion of catheter tip 102; FIG. 5D shows a side view of catheter tip 102 properly positioned over access needle 107 for penetrating into a blood vessel (e.g., vein); and FIG. 5E is a magnified view of a segment "S5E" of FIG. 5D. Similar to previous examples, catheter 100 includes an elongated tubular catheter body 101 enclosing lumen 118 which extends throughout its length along longitudinal axis 114, the catheter is configured for passing over an access needle (e.g., needle 107) into a blood vessel. Catheter body 101 includes catheter tip 102 that ends with distal edge 111 forming opening 119 to the lumen 118 between top portion 112 and bottom portion 113.

In this exemplary configuration, distal edge 111 includes a front edge portion 120, extending from top portion 112 towards bottom portion 113, which is substantially perpendicularly to longitudinal axis 114. Distal edge 111 also includes an at least one inclined edge portion 130 which at least in part thereof (e.g., along most or substantially all length thereof, as shown) is substantially parallel in contour or boundary to longitudinal axis 114. Front edge portion 120 merges with inclined edge portion 130 at curved merging portions located inferiorly to longitudinal axis 114, optionally in close proximity to the relative height level of bottom portion 113. In some embodiments, catheter tip 102 is tapered and decreases in outer diameter and/or in thickness towards distal edge 111, in order to ease penetration of the catheter into the skin and to the blood vessel.

Catheter 100 is configured to engage an inner surface of the blood vessel (as shown in FIGS. 2, for example) with inclined edge portion 130 when pushed over access needle 107, and to slide with inclined edge portion 130 distally on the inner surface of the blood vessel when catheter tip 102 is pressed against the blood vessel wall with the access needle withdrawn relative thereto. Optionally, catheter 100 is configured to first engage the inner surface of the blood vessel with the inclined edge portion 130 proximally to the access needle 107.

Inclined edge portion 130 includes two sliding surfaces 131 and 132 provided at different sides of longitudinal axis 114. Sliding surfaces 131 and 132 are substantially flat along at least most surface area thereof, and both extend along a shared plane parallel to longitudinal axis 114, parallel to the plan view (e.g., top or bottom view, as shown in FIG. 5B) and perpendicular to the elevation view (e.g., side view, as shown in FIG. 5A) of catheter 100. In common practice of peripheral IV access, after penetrating into the blood vessel, the catheter is usually then further advanced distally in a shallow angle almost parallel to the blood vessel inner surface. The potential advantage of this design feature of inclined edge portion 130 is therefore two-fold: (a) unlike catheters with inclined and/or cone-shaped tip inherently encourage catheter advancing in a greater angle towards the inner surface of the blood vessel, inclined edge portion 130 is substantially parallel to catheter longitudinal axis 114 hence inherently encourages axial sliding motion over blood vessel inner surface, and/or (b) unlike known catheters which are commonly configured with rounded edge and/or small footprint, inclined edge portion 130 has substantially greater footprint with sliding surfaces 131 and 132, also being flat and smooth, hence provides reduced traction and increased gliding potential on the blood vessel inner surface.

Each one of the sliding surfaces 131 and 132 distinctly merges with front edge portion 120: first sliding surface 131 merges at a first merging portion 133, and second sliding surface 132 merges at a second merging portion 134. Merging portions 133 and 134 are provided at different sides of longitudinal axis 114 and are transversely remote therefrom, therefore reducing likelihood of dissecting blood vessel wall tissue following unintentional puncturing of the blood vessel wall on its inner surface with needle tip 108, unlike other catheters that can engage with the formed puncture with a single edge portion adjacent needle tip 108 and provided on longitudinal axis 114, which can further expand the puncture and eventually dissect the tissue. Each one of merging portions 133 and 134 is curved and/or inclined, for allowing smooth transitioning of catheter 100 from a greater angle to a shallower angle relative to blood vessel axis, when merging portions 134 and/or 135 directly engage with blood vessel inner surface. Inclined edge portion 130 also includes a single inclined edge portion 121 at the merging of both sliding surface 131 and 132 with bottom portion 113. Inclined edge portion 121 extends from bottom portion 113 inclined to the longitudinal axis 114 towards front edge portion 120.

Figure 6A:
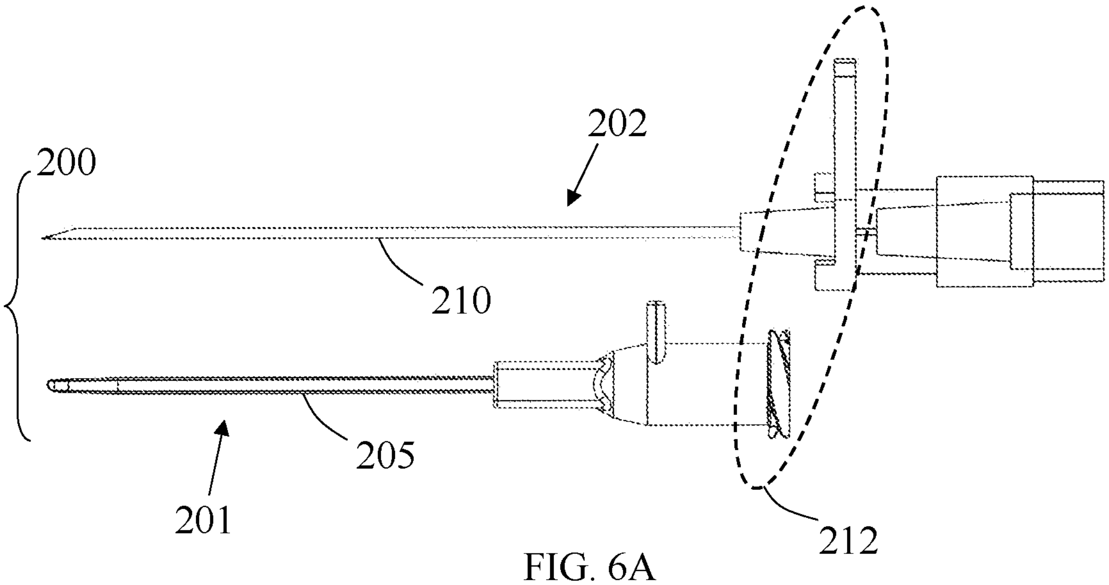
FIGS. 6A-6C illustrate views of an exemplary vascular access kit, according to some embodiments.
Figure 6B:
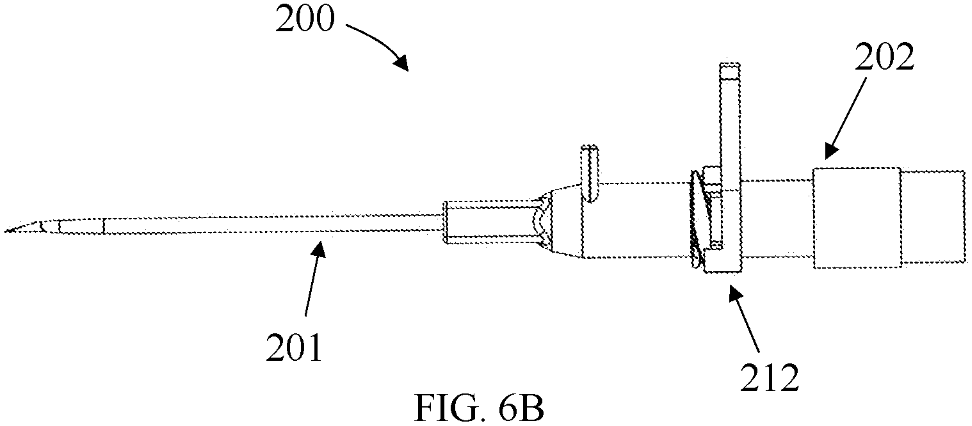
Figure 6C:
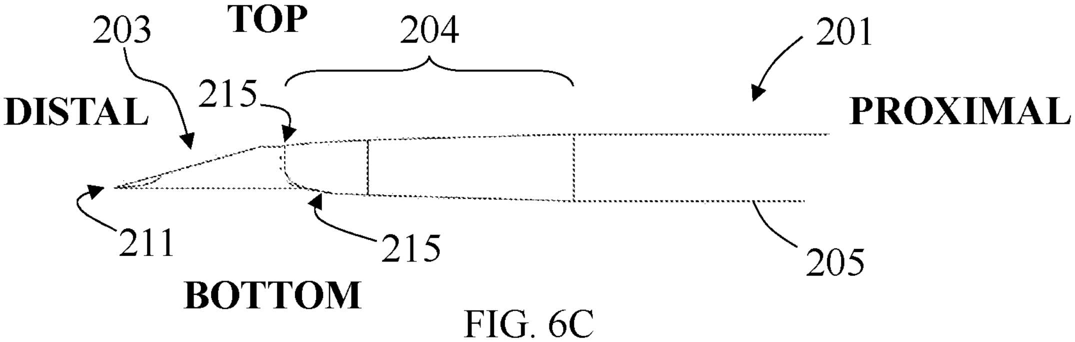
Figure 7A:
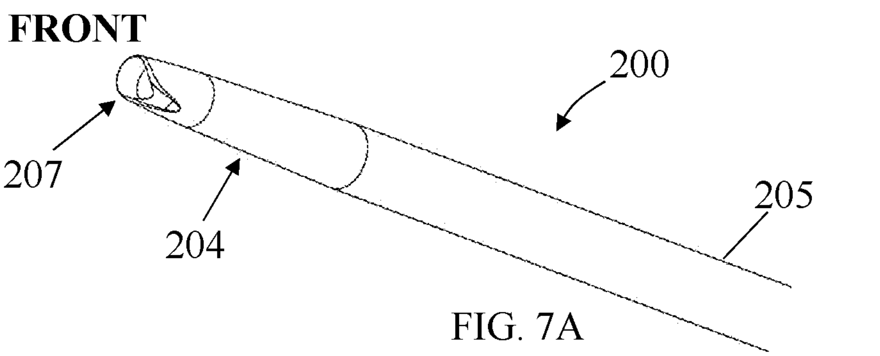
FIGS. 7A-7C illustrate views of an exemplary vascular access catheter of the kit shown in FIG. 6A, according to some embodiments.
Figure 7B:
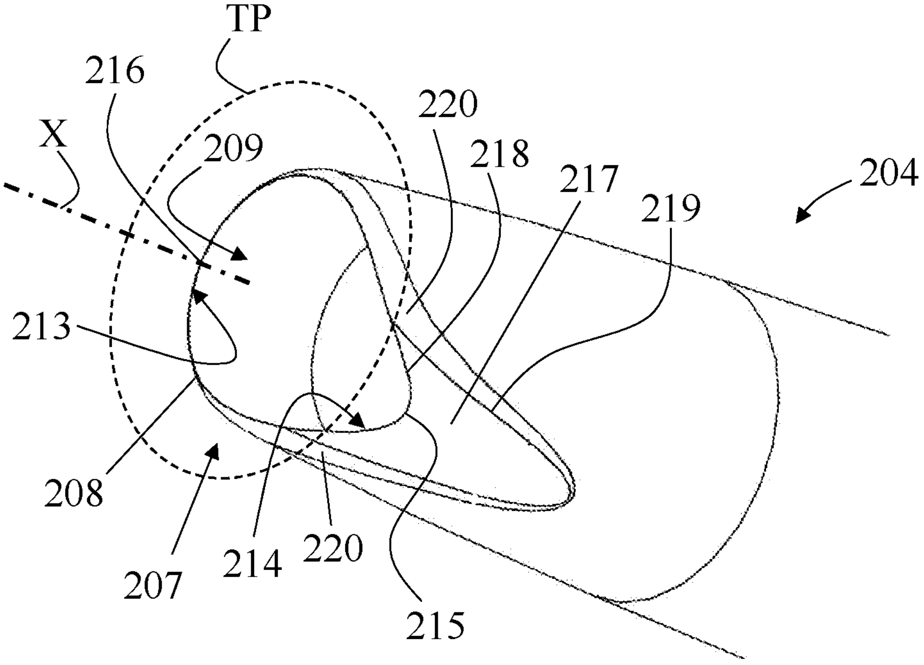
Figure 7C:
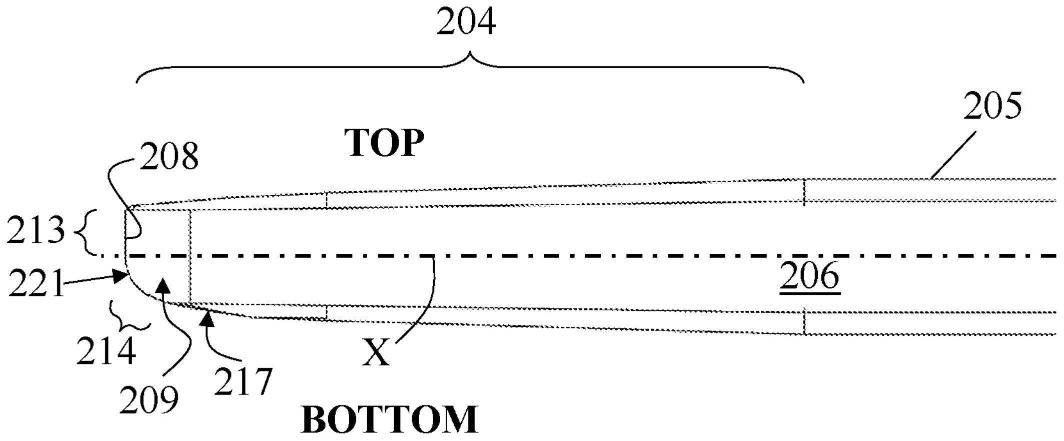

FIGS. 6A-6C illustrate views of an exemplary vascular access kit 200 comprising at least a vascular access catheter 201 and an access needle 202. FIG. 6A shows catheter 201 and access needle 202 separated, and FIG. 6B shows access needle 202 extending through catheter 201 and fixedly connected thereto in a predetermined relative lengthwise position. FIG. 6C shows an enlarged (zoom-in) view of a distal portion of kit 200 in FIG. 6B, showing beveled tip 203 of access needle 202 and catheter tip 204 of catheter 201. FIGS. 7A-7C illustrate views of catheter 201 including a partial isometric view of a distal length of catheter 201 showing part of catheter body with catheter tip 204 (FIG. 7A), an enlarged view showing front portion of catheter tip 204 (FIG. 7B), and a side cross sectional view of a distal length of catheter 201 including catheter tip 204 (FIG. 7C).

Catheter 201 includes an elongated tubular catheter body 205 enclosing a lumen 206. Lumen 206 is cylindrical along a portion (e.g., most) of catheter body 205 proximally to catheter tip 204 and tapers along a portion of catheter tip 204. Catheter tip 204, which is the front (distal) portion of catheter body 205, ends with a catheter distal end 207 and comprising a distal edge 208 at the catheter distal end 207 surrounding an opening 209 opened to lumen 206. Access needle 202 includes a hollow needle body 210 and a needle beveled tip 203 that ends with a distal sharp needle edge 211. Catheter 201 is configured to accommodate access needle 202 through lumen 206 and opening 209 in at least two configurations comprising a 'tissue-penetration configuration' (shown in FIGS. 6B, 8A and 9A, for example) wherein beveled tip 203 fully extends from lumen 206 distally to catheter distal end 207, and a 'safety configuration' (shown in FIGS. 8B and 9B, for example) wherein beveled tip 203 fully resides within lumen 206 proximally to catheter distal end 207. Lumen 206 decreases in diameter along catheter tip 204 to a sealing diameter smaller than a diameter of access needle proximally to beveled tip 203, so as to form a seal around access needle 202 for preventing blood from accessing into lumen 206 via opening 209 when in the tissue-penetration configuration, and to facilitate access of blood into lumen 206 via opening 209 when in the safety configuration. Catheter 201 and access needle 202 includes mating portions of coupling means 212, optionally in a form of luer fitting as shown, configured to fixate access needle 202 in catheter 201 in the tissue-penetration configuration.

Distal edge 208 includes a front edge portion 213 spanning a top portion of opening 209, and an inclined edge portion 214 spanning a bottom portion of opening 209 and inclining (towards bottom end of catheter tip 204) proximally away from front edge portion 213, relative to a longitudinal axis X of catheter body 201. The top portion of opening 209 relates to the cross-sectional area of opening 209 above longitudinal axis X, and the bottom portion of opening 209 relates to the cross-sectional area of opening 209 below longitudinal axis X (as shown in FIG. 7C). Front edge portion 213 substantially coincides with a transverse plane TP of catheter body 205 crossing perpendicularly to longitudinal axis X. Optionally, front edge portion 213 spans at least half of a cross section of catheter body 205 at distal end 207. Optionally, front edge portion 213 is substantially parallel to transverse plane TP, at least in most part thereof. Inclined edge portion 214 is inclined to longitudinal axis X at an average angle greater than 20°, optionally particularly greater than 40°, optionally particularly greater than 60°, and/or is inclined to front edge portion 213 or to transverse plane TP at an average angle smaller than 45°, optionally particularly smaller than 30°, optionally particularly smaller than 20°.

In some embodiments, front edge portion 213 is at least partially flat, and inclined edge portion 214 is at least partially curved. Optionally, radius of curvature of inclined edge portion 214 is smallest adjacent to front edge portion 213 and/or greatest adjacent to a vertex 215 of inclined edge portion 214, and it optionally increases gradually between front edge portion 213 and vertex 215, optionally particularly from front edge portion 213 to vertex 215. In some embodiments, inclined edge portion 214 forms a tangential angle with longitudinal axis X smaller than about 20° adjacent to vertex 215 thereof, and/or another tangential angle with longitudinal axis X greater than about 45° adjacent to its merging portion with front edge portion 213.

In some embodiments, catheter 201 is configured to engage an inner surface of a blood vessel with inclined edge portion 214 when pushed over access needle 202, and to slide with inclined edge portion 214 distally on the inner surface of the blood vessel when catheter tip 204 is pressed against the blood vessel wall when access needle 202 is withdrawn from catheter tip 204. Prior art catheters comprising a flat front end with no significant inclining and/or curved portions can be prone to harming blood vessel wall with a bottom edge thereof acting as a sharp edge, when the catheter engages and being pushed against the blood vessel wall while being inclined relative to the blood vessel long axis. Using a curved inclined edge portion 214 can overcome this disadvantage by first reducing likelihood of harming or penetrating blood vessel wall by reducing or eliminating sharpness and/or by possessing a greater footprint area engaging the blood vessel wall. Furthermore, it can distribute a greater tangential force component in the longitudinal direction of the blood vessel lumen and a smaller normal force component directed perpendicularly towards blood vessel wall from the force applied to push the catheter, relative to prior art catheters, since that tangent of the curved inclined edge portion 214 at some or all points of contact with blood vessel wall is parallel or close to parallel to blood vessel longitudinal direction. It should be noted that distal edge 208 is not fully inclined and/or curved, so that it includes a significantly sized front edge portion 213 for preserving sufficient structural integrity of catheter tip 204 during penetration through skin tissue and/or into a blood vessel on access needle 202 in the tissue-penetration configuration.

Inclined edge portion 214 includes or merges with a sliding surface 217. Sliding surface 217 is optionally at least partially curved and/or flat, and is at least partially parallel, or inclined at a shallow angle (e.g., smaller than 45°, optionally particularly smaller than 20°), to inclined edge portion 214 and/or to longitudinal axis X. Sliding surface 217 forms a shaped area bounded by and between a distal parabola 218 and a proximal parabola 219, such that distal parabola 218 has a smaller focal length than proximal parabola 219. In some embodiments, when kit 200 is assembled in the tissue-penetration configuration, needle edge 211 has an equal or greater distance to vertex 215 of inclined edge portion 214 (which is the vertex of distal parabola 218) than to a vertex 216 of front edge portion 213, shown in FIG. 6C. In some embodiments, catheter tip 204 varies in thickness along sliding surface 217, and sliding surface 217 has an average radius of curvature substantially greater than a radius of an outer surface portion of catheter tip opposing sliding surface 217 in a mutual transverse cross section. In some embodiments, sliding surface 217 has elastic resistance to inward radial deformation smaller than an opposing potion (along the top end) of the catheter tip 204. In some embodiments, kit 200 is configured such that catheter tip 204, along a bottom portion or end thereof, when radially inwardly collapsed, has a footprint on a surface of a blood vessel wall greater in size than a maximal sized lesion formable in the blood vessel wall by access needle 202.

Besides preventing harm to blood vessel wall by engaging the blood vessel inner surface with the curved inclined edge portion 214, catheter tip 204 is optionally also configured to reduce likelihood to increase size and/or severity of a lesion already caused such as by unintentional blood vessel wall penetration with sharp needle edge 211, when kit 200 is fixated at the tissue-penetration configuration, such as by expanding puncture size and/or advancing catheter 201 through this puncture out of blood vessel lumen. Inclined edge portion 214 includes two curved surfaces 220 provided at opposite sides of opening 209 relative to longitudinal axis X, each one of sliding surfaces 220 distinctly merges with front edge portion 213 at a different merging portion 221. This way, when catheter tip 204 engages a preformed lesion, the initial contact and sliding across the lesion will occur directly with the siding surfaces 220 that are more distant than the lesion width (being equal to or smaller than diameter of access needle 202). Each merging portion 221 is optionally rounded, curved and/or inclined, and is optionally located adjacent to or below longitudinal axis X.

Figure 8A:
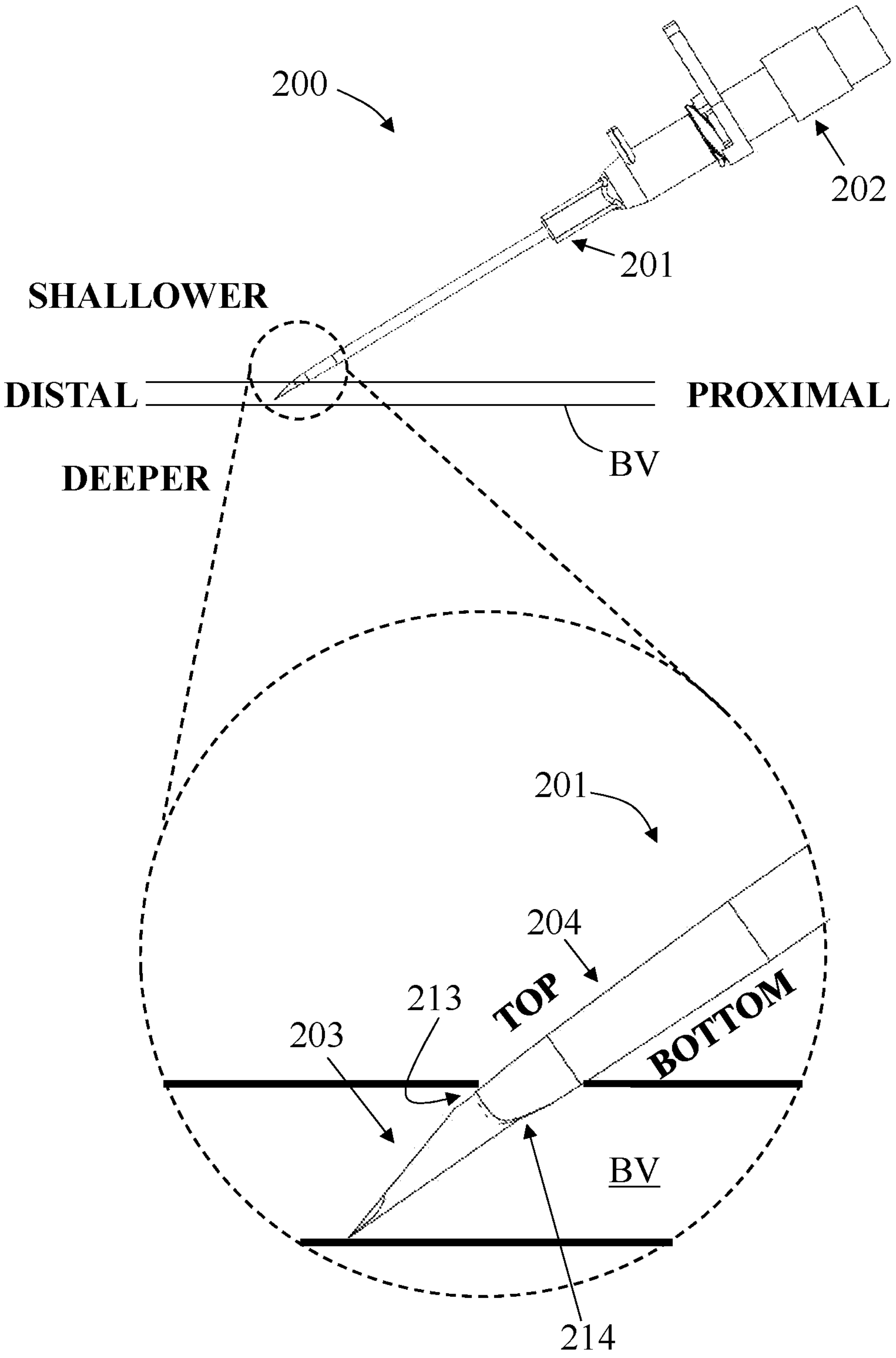
FIGS. 8A-8E schematically illustrate a first set of exemplary scenarios representing steps in a method for accessing a blood vessel using the kit shown in FIG. 6A, according to some embodiments.

FIGS. 8A-8E schematically illustrate a first set of exemplary scenarios representing steps in a method for accessing (inserting catheter 201 into) blood vessel BV using kit 200. As shown in FIG. 8A, catheter 201 and access needle 202 of kit 200 are first assembled and fixated together in the tissue-penetration configuration, and then pushed through skin layers of a live subject until penetrating blood vessel BV with beveled tip 203 to allow blood drawing into access needle 202 from blood vessel BV. Size of kit 200 is determined according to blood vessel dimensions so that by correctly positioning beveled tip 203 in lumen of blood vessel BV in the tissue-penetration configuration, catheter tip 204 is inserted (e.g., mostly or fully) into blood vessel BV as well. Catheter insertion can include verifying that bottom portion of opening 209 or catheter tip 204 is directed towards blood vessel BV, and/or that top portion of opening 209 or catheter tip 204 is directed away from blood vessel BV, for indicating correct positioning and orientation. When properly penetrating through skin and into blood vessel BV, for example as shown, top portion of front edge portion 213 functions as catheter's leading edge while inclined edge portion 214 is sufficiently remote proximally so as to diminish or avoid significant contribution to physical interaction with surrounding tissues during catheter insertion relative to contribution of front edge portion 213.

Figure 8B:
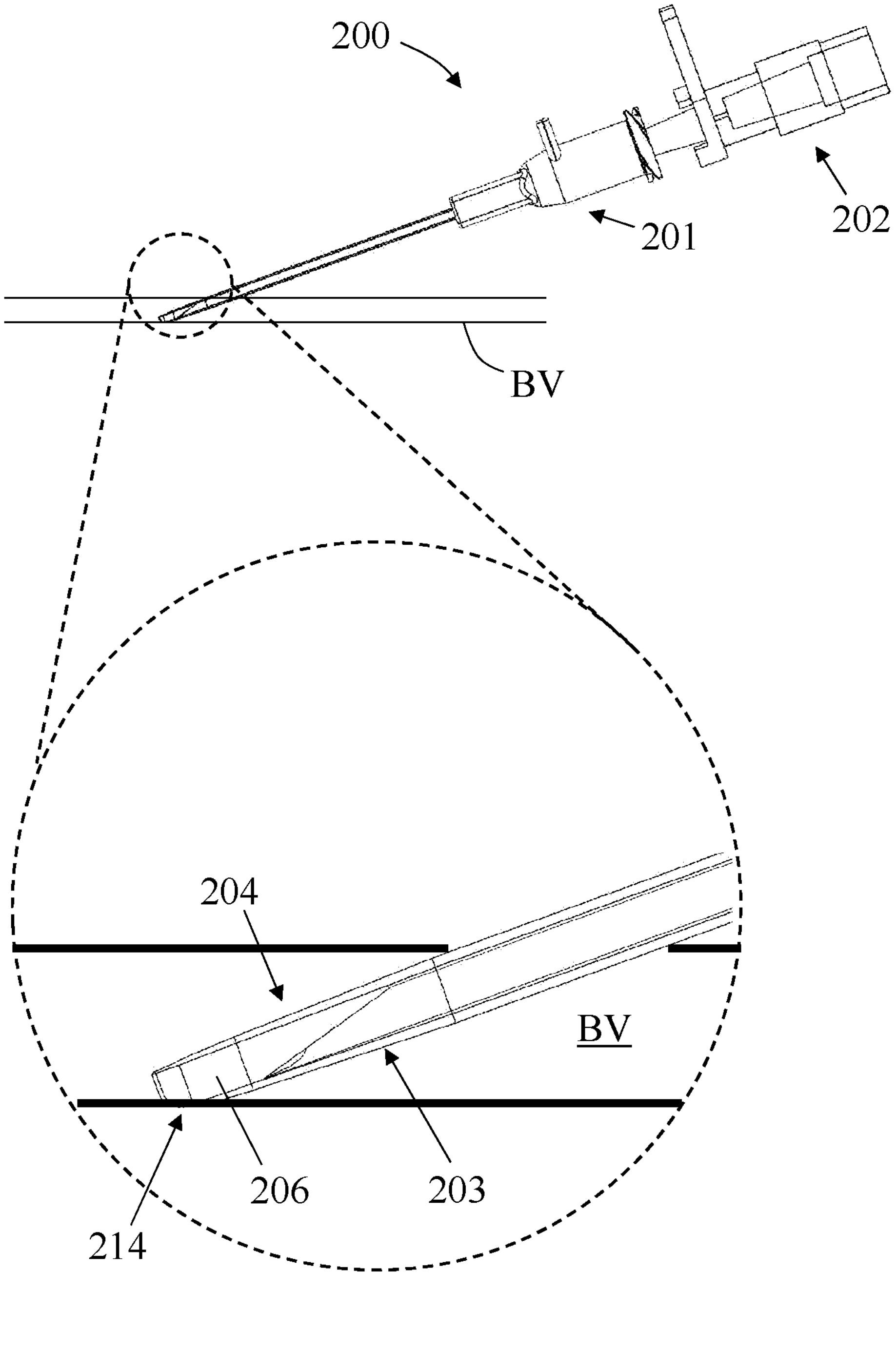

Once beveled tip 203 is in lumen of blood vessel BV, the medical practitioner can verify blood is drawn from blood vessel BV into access needle 202 which can indicate proper positioning of beveled needle 203. Following that, catheter 201 and access needle 202 can be shifted to the safety configuration (as shown in FIG. 8B) such as by moving beveled tip 203 relative to catheter tip 204 wherein beveled tip 203 fully resides within lumen 206 proximally to catheter distal end 207. This shifting step can follow or include change of inclination of catheter 201 with access needle 202 relative to blood vessel BV and/or repositioning of catheter 201 and/or access needle 202 in blood vessel BV.

Figure 8C:
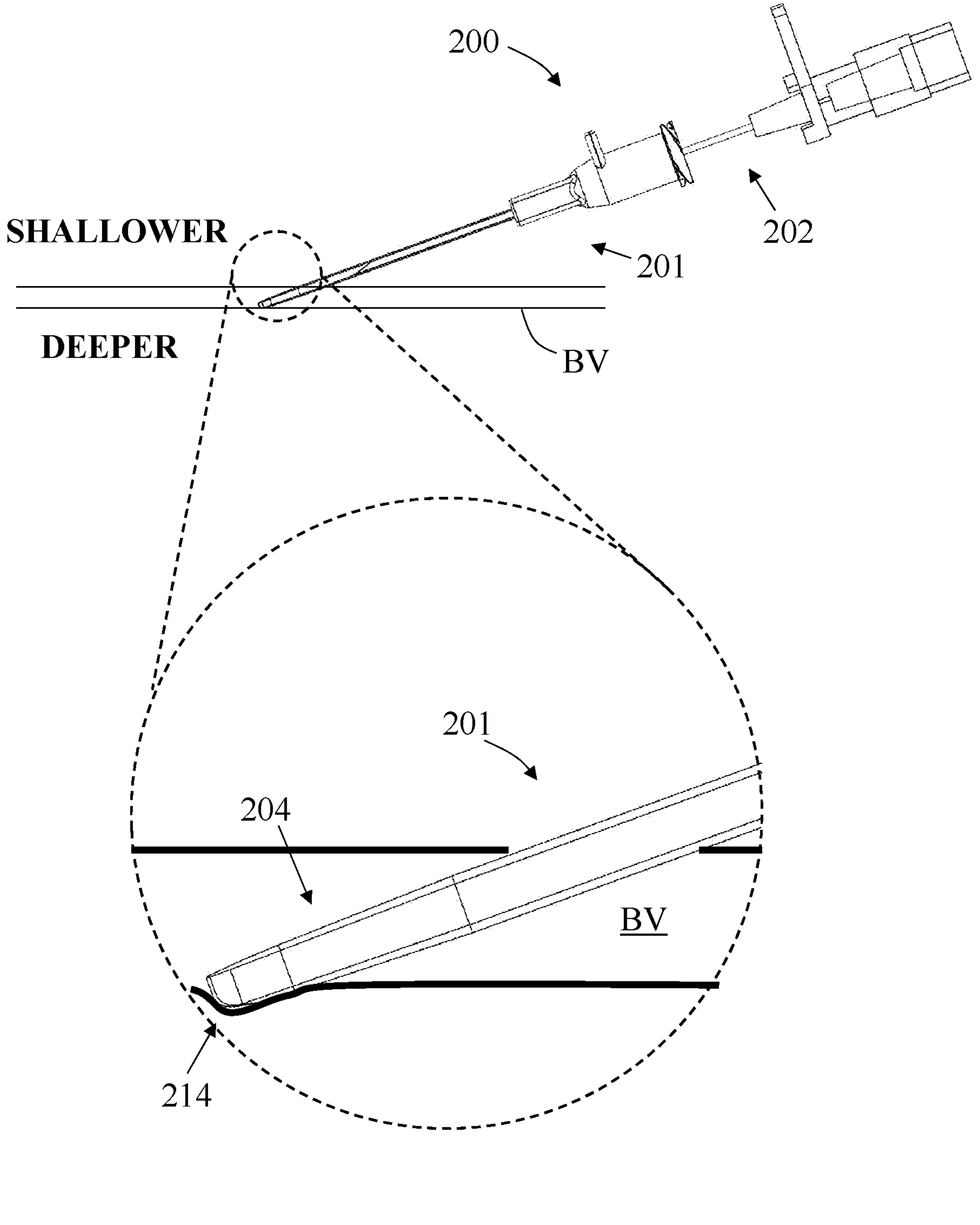
Figure 8D:
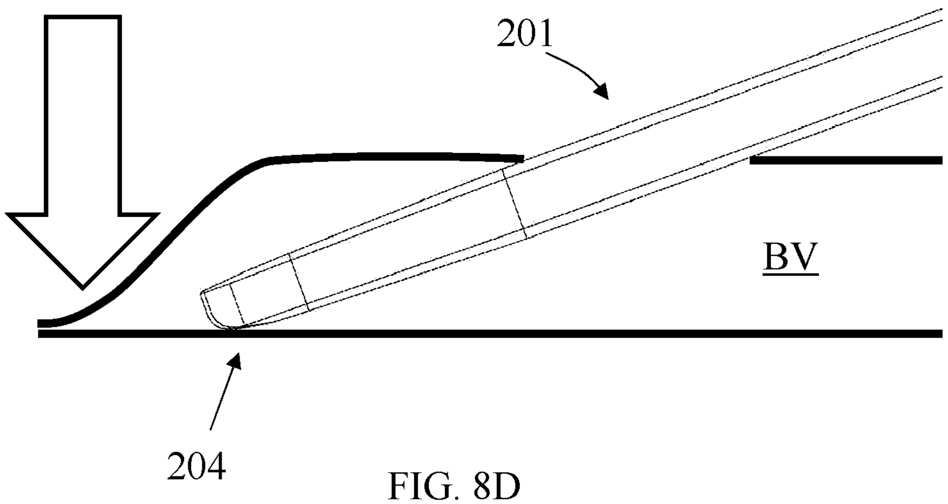
Figure 8E:
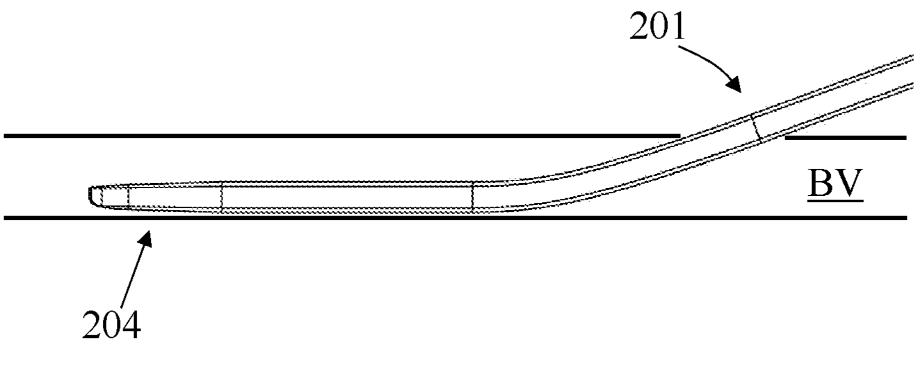

When in the safety configuration, the medical practitioner can verify that blood is drawn from blood vessel BV into lumen 206 of catheter 201 before proceeding to complete its deployment. Then, access needle 202 can be further withdrawn and/or catheter 201 can be pushed forward (distally) over needle 202, and this can include engaging an inner (e.g., deeper) surface of blood vessel BV with inclined edge portion 214, as shown in FIG. 8C. Access needle 202 can be removed completely from lumen 206 and optionally replaced with a fluid source such as syringe connectable to catheter 201 with coupling means 212, which may be used to flush the catheter and/or to administer medication into blood vessel BV via catheter 201. Access needle 202 removal and/or syringe coupling can be performed while compressing blood vessel BV distally to catheter tip 204, as shown in FIG. 8D. Catheter 201 can then be advanced distally in the blood vessel (FIG. 8E) to final positioning and deployment.

Figure 9A:
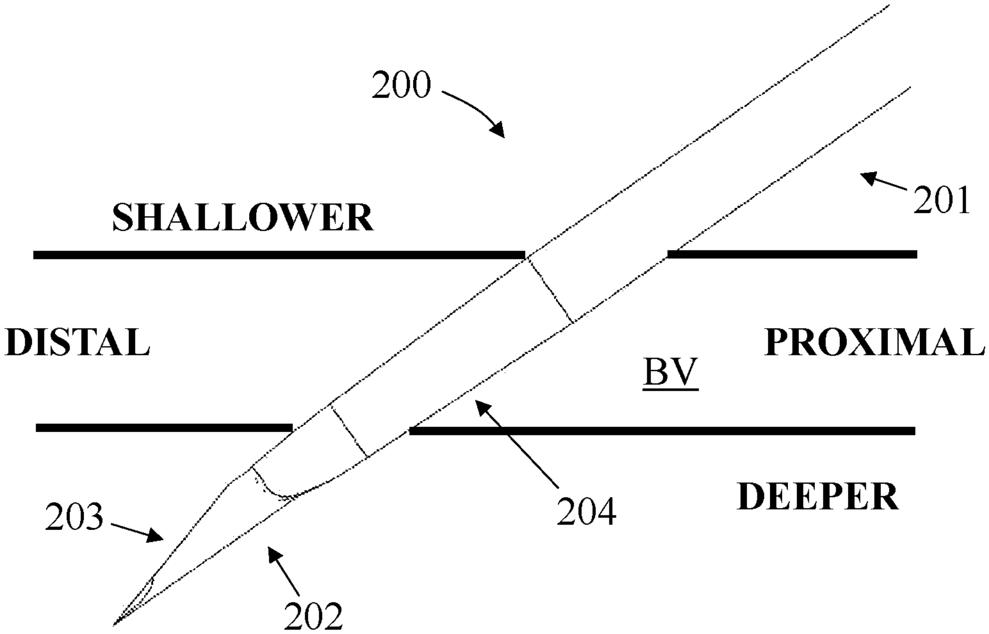
FIGS. 9A-9F schematically illustrate a second set of exemplary scenarios representing steps in a method for accessing a blood vessel using the kit shown in FIG. 6A, according to some embodiments.
Figure 9B:
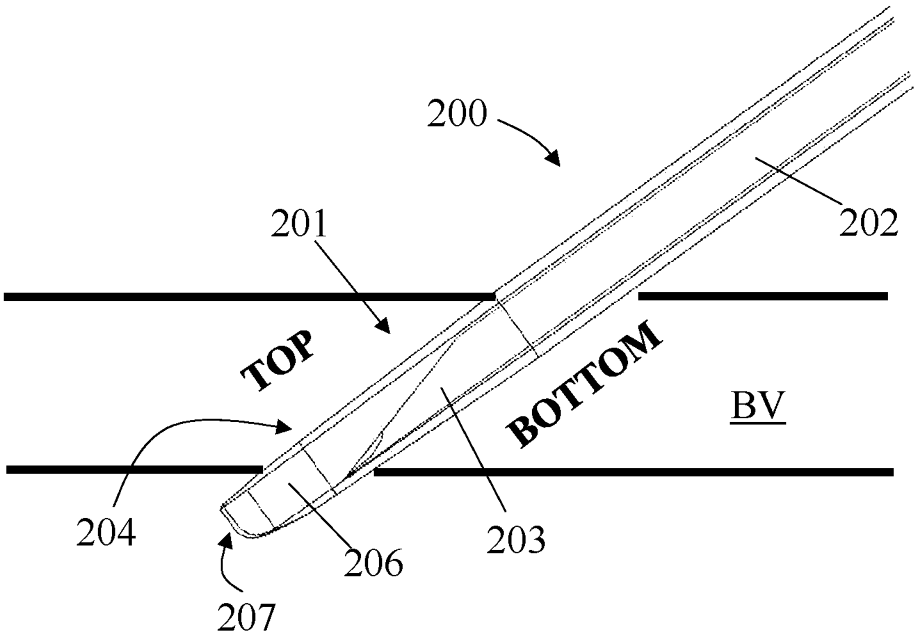
Figure 9C:
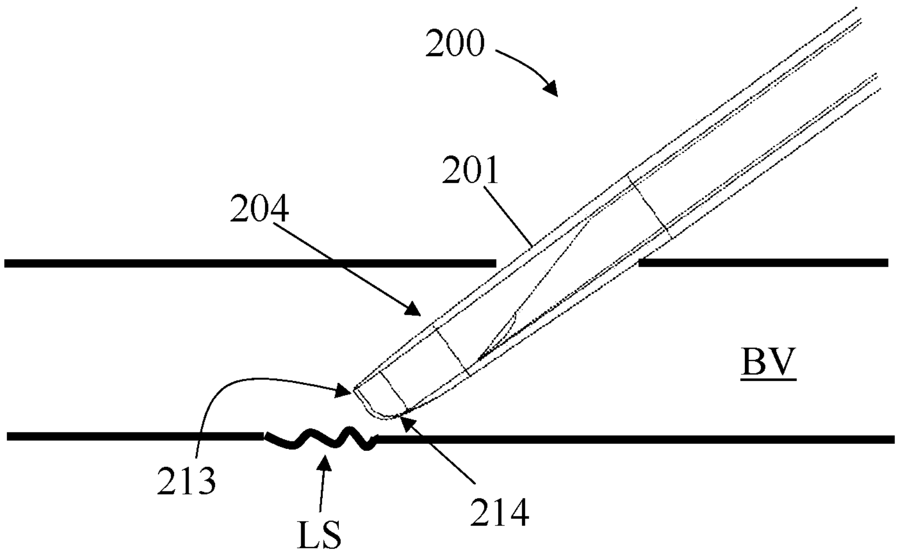
Figure 9D:
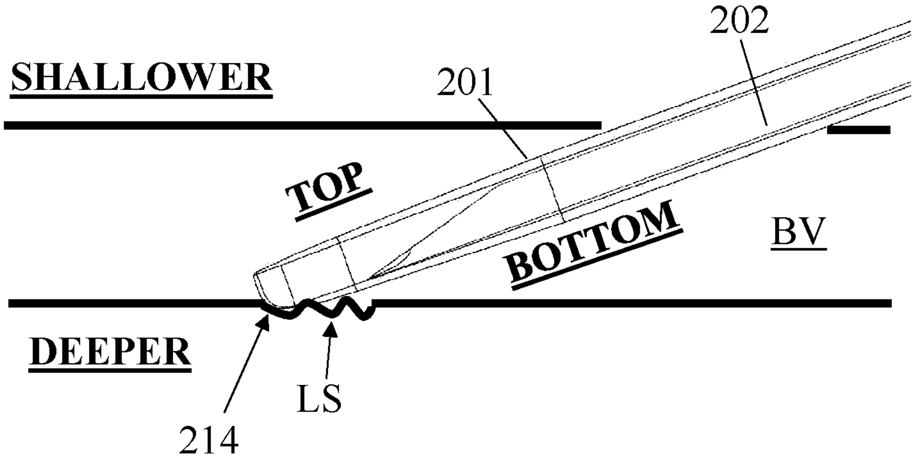
Figure 9E:
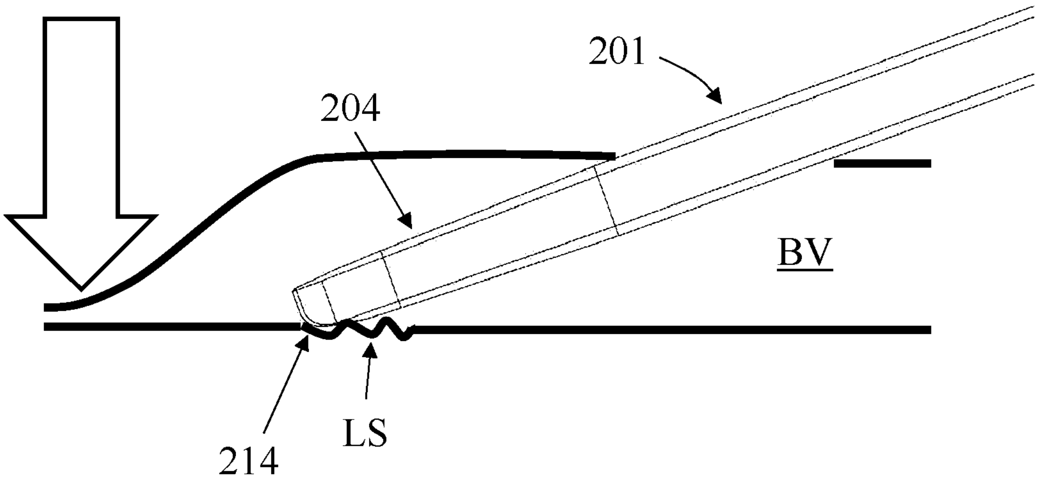

FIGS. 9A-9F schematically illustrate a second set of exemplary scenarios representing steps in a method for accessing blood vessel BV using kit 200. In this set of scenarios, the medical practitioner can knowingly (e.g., intentionally) or unknowingly push the access needle 202 with catheter 201 in the tissue-penetration configuration across entire width of blood vessel BV such that beveled tip 203 penetrates both a top (shallow) portion and an opposing bottom (deep) portion of blood vessel BV, as shown in FIG. 9A for example. In this example, inserting catheter tip 204 into blood vessel BV when in the tissue-penetration configuration includes or results in forming a lesion LS through the inner surface of blood vessel BV wall with beveled tip 203 (shown in FIG. 9C, for example). Afterwards, catheter 201 can be withdrawn back into lumen of blood vessel BV until reaching and/or validating correct positioning before proceeding to final deployment stages of catheter 201 in blood vessel BV. Before withdrawing catheter 201, access needle 202 can be partially withdrawn (e.g., to the safety configuration) or fully withdrawn (e.g., removed) from catheter 201.

Figure 9F:
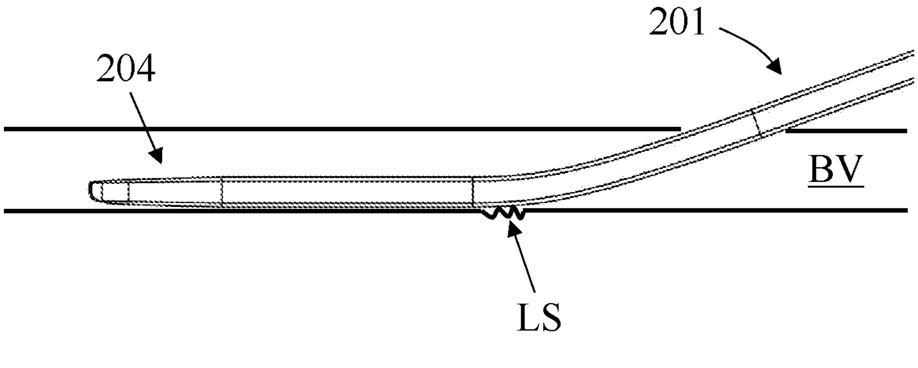

Following the 'through-and-through' penetration of blood vessel BV as shown in FIG. 9A, the medical practitioner can first verify if blood is drawn from blood vessel BV into access needle 202, although in this scenario the verifying can result in annulling that blood was drawn into the access needle (i.e., indicating or proving that no blood was actually drawn from blood vessel BV into access needle 202). With such a result, catheter 201 and access needle 202 can first be shifted to the safety configuration (FIG. 9B), or alternatively access needle 202 is removed from catheter 201, and then catheter 201 can be gradually withdrawn optionally with access needle 202 maintained in the safety configuration (FIG. 9C), until verifying blood is drawn from blood vessel BV into lumen 206 (indicating or proving that catheter tip 204 has been inserted into blood vessel BV). Catheter 201 can then be pushed and engage the inner surface of blood vessel BV with inclined edge portion 214 (FIG. 9D), optionally by sliding over remote portions of the inner surface of blood vessel BV from opposite sides of lesion LS with sliding surfaces 220 of inclined edge portion 214, for passing across lesion LS without penetrating again therethrough or harming surrounding tissue. If not already done at an earlier stage, access needle 202 can be completely removed from lumen 206 of catheter 201 (FIG. 9E), and catheter 201 can be advanced distally to a chosen deployment positioning (FIG. 9F). Advancement of catheter 201 can optionally include sliding over and across lesion LS with inclined edge portion 214 and/or catheter tip 204 along a bottom end thereof including with sliding surface 217.

In some embodiments, an advantage of using catheter 201 and/or kit 200 can be particularly met for accessing diseased or very small veins. In a small vein the diameter at the access point may be about the size the catheter body or even smaller, therefore at any given time along the access and deployment process there can be at least some engagement by a distal edge or portion of a prior art catheter tip with the blood vessel wall. By applying catheter 201 having inclined edge portion 214, this results in a smaller relative height than with standard catheter during inclined penetrations into the blood vessel. In some such embodiments, a preliminary step in a method for using kit 200 to deploy catheter 201 may include verifying that the blood vessel is diseased and/or is a vein equal to or smaller in diameter than catheter body or than about 1 mm.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step (s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. A vascular access kit, comprising:

(a) a vascular access catheter comprising:

an elongated tubular catheter body enclosing a lumen, wherein the catheter body includes a catheter tip ending with a catheter distal end and comprising a distal edge at the catheter distal end surrounding an opening opened to the lumen; and (b) an access needle comprising a hollow needle body and a beveled tip ending with a distal sharp needle edge;

wherein the vascular access catheter is configured to accommodate the access needle through the lumen and the opening;

wherein the distal edge includes a front edge portion comprising a flat front surface in longitudinal cross section forming the distal tip of the catheter, the flat front surface extending in a transverse plane that is substantially perpendicular to a central longitudinal axis of the catheter body, the flat front surface spanning a top portion of the opening;

wherein the distal edge further includes an inclined edge portion spanning a bottom portion of the opening merging with and inclining proximally away from the flat front surface of the front edge portion relative to the central longitudinal axis of the catheter body;

wherein the inclined edge portion of the opening is at least partially convexly curved in longitudinal cross section relative to the central longitudinal axis of the catheter body to form or merge with a sliding surface extending proximally along and from the bottom portion of the opening; and wherein the sliding surface has elastic resistance to inward radial deformation smaller than an opposing top portion of the catheter tip.

2. The kit according to claim 1, wherein the vascular access catheter is configured to accommodate the access needle through the lumen and the opening in at least two configurations comprising a tissue-penetration configuration wherein the beveled tip fully extends from the lumen distally to the catheter distal end, and a safety configuration wherein the beveled tip fully resides within the lumen proximally to the catheter distal end.

3. The kit according to claim 2, wherein the lumen decreases in diameter along the catheter tip to a sealing diameter smaller than a diameter of the access needle proximally to the beveled tip, so as to form a seal around the access needle for preventing blood from accessing the lumen via the opening when in the tissue-penetration configuration and to facilitate access of blood into the lumen via the opening when in the safety configuration.

4. The kit according to claim 2, comprising a coupler configured to fix the access needle in the catheter in the tissue-penetration configuration.

5. The kit according to claim 2, wherein when in the tissue-penetration configuration, a distance from the distal sharp needle edge to a vertex of the inclined edge portion is equal to or greater than a distance from the distal sharp needle edge to a vertex of the front edge portion.

6. The kit according to claim 1, wherein the bottom portion of the catheter tip is configured to radially inwardly collapse to form a footprint on a surface of the blood vessel wall greater than a maximum lesion configured to be formed in the blood vessel wall by the access needle.

7. A method for inserting a catheter into a blood vessel using the kit of claim 2, the method comprising:

inserting the catheter tip into the blood vessel when the catheter and the access needle are in the tissue-penetration configuration;

shifting the vascular access catheter and the access needle to the safety configuration by moving the beveled tip relative to the catheter tip, such that the beveled tip fully resides within the lumen proximally to the catheter distal end;

engaging an inner surface of the blood vessel with the inclined edge portion;

removing the access needle from the lumen; and advancing the vascular access catheter distally in the blood vessel.

8. The method according to claim 7, wherein the inserting includes forming a lesion through the inner surface of the blood vessel wall with the beveled tip, wherein the engaging includes sliding over remote portions of the inner surface from opposite sides of the lesion with the inclined edge portion, and wherein the advancing includes sliding over and across the lesion with one or both of the inclined edge portion or the catheter tip along a bottom portion thereof.

9. The method according to claim 7, comprising verifying if blood is drawn from the blood vessel into the access needle.

10. The method according to claim 9, wherein, if the verifying results in annulling that blood is drawn into the access needle, the shifting is followed by withdrawing the vascular access catheter until verifying blood is drawn from the blood vessel into the lumen.

11. The method according to claim 10, wherein the withdrawing precedes the engaging.

12. The method according to claim 7, wherein the engaging follows verifying blood is drawn from the blood vessel into the lumen after the shifting.

13. The method according to claim 7, wherein the inserting includes:

verifying the vascular access catheter is fixated to the access needle in the tissue- penetration configuration;

penetrating the blood vessel with the beveled tip to allow blood drawing into the access needle from the blood vessel.

14. The method according to claim 7, wherein the inserting includes verifying at least one of that the bottom portion is directed towards the blood vessel, or that the top portion is directed away from the blood vessel.

15. The method according to claim 7, wherein the inserting step includes or is followed by a step of verifying that the blood vessel is one or more of (1) diseased, (2) a vein having a diameter equal to or smaller than the diameter of the catheter body, or (3) a vein having a diameter equal to or smaller than 1 mm.

16. A vascular access kit, comprising:

(a) a vascular access catheter comprising:

an elongated tubular catheter body enclosing a lumen defining a central longitudinal axis, wherein the catheter body includes a catheter tip ending with a catheter distal end and comprising a distal edge at the catheter distal end surrounding an opening opened to the lumen; and (b) an access needle comprising a hollow needle body and a beveled tip ending with a distal sharp needle edge;

wherein the vascular access catheter is configured to accommodate the access needle through the lumen and the opening;

wherein the distal edge includes a front edge portion forming the distal tip of the catheter spanning a top portion of the opening and an inclined edge portion spanning a bottom portion of the opening and inclining proximally away from the front edge portion, relative to the central longitudinal axis of the catheter body;

wherein the front edge portion is substantially flat and substantially parallel to a transverse plane that is perpendicular to the central longitudinal axis, and wherein the substantially flat front edge portion extends substantially perpendicular to the central longitudinal axis from the top portion of the opening downward to or beyond the central longitudinal axis of the lumen;

wherein the inclined edge portion of the opening merges with the substantially flat front edge portion and is at least partially convexly curved in longitudinal cross section relative to the central longitudinal axis of the catheter body to further form or merge with a sliding surface extending proximally along and from the bottom portion of the opening, and wherein the radius of curvature of the inclined edge portion increases as it inclines proximally away from the front edge portion to the sliding surface.

17. The kit according to claim 16, wherein the bottom portion of the catheter tip is configured to radially inwardly collapse to form a footprint on a surface of the blood vessel wall greater than a maximum lesion configured to be formed in the blood vessel wall by the access needle.

18. A vascular access kit, comprising:

(a) a vascular access catheter comprising:

an elongated tubular catheter body enclosing a lumen defining a central longitudinal axis, wherein the catheter body includes a catheter tip ending with a catheter distal end and comprising a distal edge at the catheter distal end surrounding an opening opened to the lumen; and (b) an access needle comprising a hollow needle body and a beveled tip ending with a distal sharp needle edge;

wherein the vascular access catheter is configured to accommodate the access needle through the lumen and the opening;

wherein the distal edge includes a front edge portion comprising a flat front surface in longitudinal cross section forming the distal tip of the catheter, the flat front surface extending in a transverse plane that is substantially perpendicular to the central longitudinal axis of the catheter body, the flat front surface spanning a top portion of the opening;

an inclined edge portion spanning a bottom portion of the opening and inclining proximally away from the front edge portion, relative to the central longitudinal axis of the catheter body;

wherein the inclined edge portion of the opening merges with the flat front edge portion and is at least partially convexly curved in longitudinal cross section relative to the central longitudinal axis of the catheter body, and wherein the inclined edge portion includes or merges with a sliding surface extending proximally along a bottom portion of the tubular catheter body, and wherein the sliding surface comprises one or more of a groove, a slit, a weakened portion, or a flattened portion configured to deform radially inward with an elastic resistance to inward radial deformation smaller than a top portion of the tubular catheter body to facilitate the vascular access catheter sliding along an inner wall of a blood vessel without damaging the inner wall of the blood vessel when the vascular access catheter is introduced into the blood vessel over the access needle.

19. The kit according to claim 18, wherein the front edge portion substantially coincides with the transverse plane of the catheter body crossing perpendicularly to the longitudinal axis.

20. The kit according to claim 19, wherein the front edge portion spans at least half of a cross section of the catheter body at the distal end parallel to the transverse plane.

21. The kit according to claim 20, wherein a radius of curvature of the inclined edge portion is smallest adjacent to the front edge portion and greatest adjacent to a vertex of the inclined edge portion.

22. The kit according to claim 18, wherein at least a portion of the sliding surface is inclined to the longitudinal axis.

23. The kit according to claim 18, wherein the sliding surface forms a shaped area bounded by and between a distal parabola and a proximal parabola, the distal parabola has a smaller focal length than the proximal parabola.

24. The kit according to claim 18, wherein the sliding surface comprises the groove extending along a bottom end of the catheter tip, proximally from, and opened to, the inclined edge portion.

25. The kit according to claim 18, wherein the sliding surface comprises the slit extending along a bottom end of the catheter tip, proximally from, and opened to, the inclined edge portion.

26. The kit according to claim 18, wherein the sliding surface comprises the groove extending along a bottom end of the catheter tip, proximally from, and opened to, the inclined edge portion.

27. The kit according to claim 26, wherein at least a portion of the sliding surface is inclined to the longitudinal axis.

28. The kit according to claim 27, wherein the catheter tip is configured, when not internally supported with the access needle, to collapse radially inwardly when a bottom end of the catheter tip is pressed at an angle against a blood vessel wall, when the catheter body transfers to the blood vessel wall a force insufficient for causing mechanical damage thereto.

29. The kit according to claim 28, wherein the catheter is configured such that the catheter tip along a bottom end thereof, when radially inwardly collapsed, has a contact area during or immediately after collapsing on a surface of a blood vessel wall greater in size than a maximal sized cross section of the access needle.

30. The kit according to claim 18, wherein the sliding surface comprises a weakened or flattened portion.

31. The kit according to claim 30, wherein the radius of curvature of the inclined edge portion increases as it inclines proximally away from the front edge portion.

* * * * *